(12) United States Patent
Meyre et al.

(10) Patent No.: US 11,497,717 B2
(45) Date of Patent: Nov. 15, 2022

(54) NANOPARTICLES FOR USE FOR TREATING A NEURONAL DISORDER

(71) Applicant: NANOBIOTIX S.A., Paris (FR)

(72) Inventors: Marie-Edith Meyre, Saint Mande (FR); Laurent Levy, Paris (FR); Agnès Pottier, Paris (FR)

(73) Assignee: NANOBIOTIX S.A., Paris (FR)

( * ) Notice: Subject to any disclaimer, the term of this patent is extended or adjusted under 35 U.S.C. 154(b) by 69 days.

(21) Appl. No.: 16/955,092

(22) PCT Filed: Dec. 18, 2018

(86) PCT No.: PCT/EP2018/085593
§ 371 (c)(1),
(2) Date: Jun. 18, 2020

(87) PCT Pub. No.: WO2019/121748
PCT Pub. Date: Jun. 27, 2019

(65) Prior Publication Data
US 2021/0015756 A1 Jan. 21, 2021

(30) Foreign Application Priority Data

Dec. 19, 2017 (EP) .................................. 17306826

(51) Int. Cl.
| A61K 9/51 | (2006.01) |
| A61P 25/28 | (2006.01) |
| A61P 25/16 | (2006.01) |
| A61K 33/24 | (2019.01) |

(52) U.S. Cl.
CPC .......... *A61K 9/5115* (2013.01); *A61K 9/5146* (2013.01); *A61K 33/24* (2013.01); *A61P 25/16* (2018.01); *A61P 25/28* (2018.01)

(58) Field of Classification Search
CPC ................................ A61K 9/5115; B82Y 5/00
See application file for complete search history.

(56) References Cited

U.S. PATENT DOCUMENTS

| 9,034,392 B2 | 5/2015 | Reed et al. |
| 2010/0113358 A1 | 5/2010 | Tezapsidis |
| 2014/0056813 A1 | 2/2014 | Pottier et al. |
| 2016/0051481 A1 | 2/2016 | Ferrari et al. |
| 2017/0290916 A1 | 10/2017 | Kaushik et al. |
| 2017/0348350 A1 | 12/2017 | Mortenson et al. |
| 2019/0351057 A1 | 11/2019 | Pottier et al. |
| 2019/0351231 A1 | 11/2019 | Meyre et al. |
| 2020/0086120 A1 | 3/2020 | Levy et al. |
| 2020/0015750 A1 | 12/2020 | Pottier et al. |

FOREIGN PATENT DOCUMENTS

| EP | 2 974 717 | 1/2016 |
| RU | 2 552 957 | 6/2015 |
| WO | WO 2009/052295 | 4/2009 |
| WO | WO 2017/060916 | 4/2017 |
| WO | WO 2018/114945 | 6/2018 |
| WO | WO 2019/121813 | 6/2019 |

OTHER PUBLICATIONS

Brambilla, D. et al. "Colloidal properties of biodegradable nanoparticles influence interaction with amyloid-β peptide" *Journal of Biotechnology*, 2011, pp. 338-340, vol. 156, No. 4.
Dante, S. et al. "Selective Targeting of Neurons with Inorganic Nanoparticles: Revealing the Crucial Role of Nanoparticle Surface Charge" *ACS Nano*, 2017, pp. 6630-6640, vol. 11, No. 7.
Xie, H. et al. "Silica nanoparticles induce alpha-synuclein induction and aggregation in PC12-cells" *Chemico-Biological Interactions*, Sep. 2016, pp. 197-204, vol. 258.
Joshi, N. et al. "Attenuation of the Early Events of α-Synuclein Aggregation: A Fluorescence Correlation Spectroscopy and Laser Scanning Microscopy Study in the Presence of Surface-Coated $Fe_3O_4$ Nanoparticles" *Langmuir*, 2015, pp. 1469-1478, vol. 31, No. 4.
Joshi, N. et al. "Supporting Information: Attenuation of the Early Events of α-Synuclein Aggregation: A Fluorescence Correlation Spectroscopy and Laser Scanning Microscopy Study in the Presence of Surface-Coated $Fe_3O_4$ Nanoparticles" *Science Letters*, 2015, pp. 1-18.
Moore, K. A. et al. "Influence of gold nanoparticle surface chemistry and diameter upon Alzheimer's disease amyloid-β protein aggregation" *Journal of Biological Engineering*, 2017, pp. 1-11, vol. 11, No. 5.
Written Opinion in International Application No. PCT/EP2018/085593, dated Apr. 3, 2019, pp. 1-12.
Allowed claims in U.S. Appl. No. 16/472,214, 2021, pp. 1-3.
Allowed claims in U.S. Appl. No. 16/472,215, 2021, pp. 1-4.
Allowed claims in U.S. Appl. No. 16/472,216, 2021, pp. 1-3.

(Continued)

*Primary Examiner* — Robert S Cabral
(74) *Attorney, Agent, or Firm* — Saliwanchik, Lloyd & Eisenschenk

(57) ABSTRACT

The present invention relates to the medical field, in particular to the treatment of neurological disorders. More specifically the present invention relates to a nanoparticle or nanoparticles' aggregate for use in prevention or treatment of a neurological disease or at least one symptom thereof in a subject without exposure of the nanoparticle or nanoparticles' aggregate to an electric field, and preferably without exposure thereof to any other external activation source, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof without exposure thereof to an electric field, and preferably without exposure thereof to any other external activation source.

9 Claims, 21 Drawing Sheets

(56) References Cited

OTHER PUBLICATIONS

Figure 1:
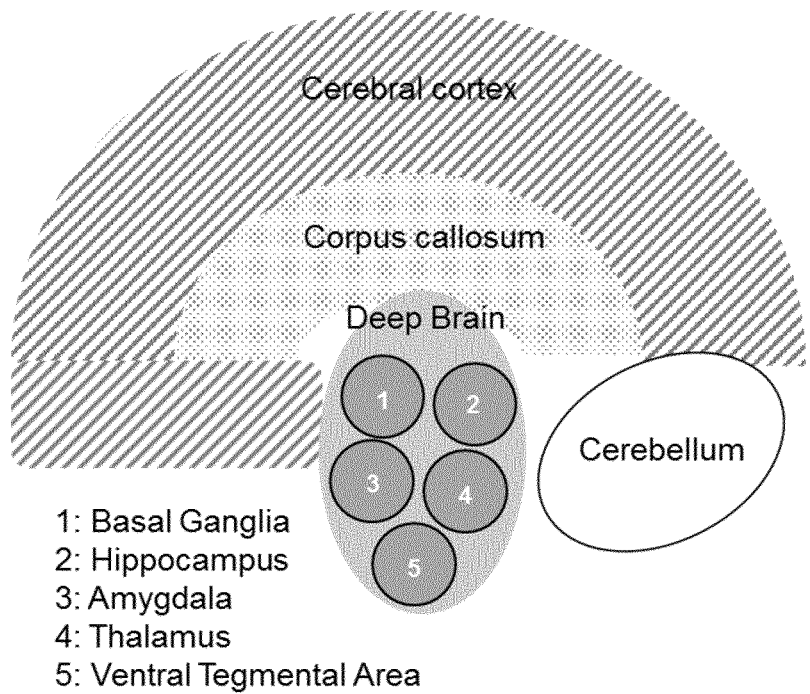

Kim, K.-M. et al. "Surface treatment of silica nanoparticles for stable and charge-controlled colloidal silica" *International Journal of Nanomedicine*, 2014, pp. 29-40, vol. 9, Suppl. 2.

Zamiri, R. et al. "Dielectrical Properties of $CeO_2$ Nanoparticles at Different Temperatures" *PLoS One*, Apr. 24, 2015, pp. 1-11, vol. 10, No. 4, e0122989.

Johnson, D. "Silicon Nanoparticles Provide Biocompatible Solution to Cancer Detection and Treatment, Porous silicon nanoparticles offer harmless diagnostic and therapeutic solution for many types of cancer" IEEE Spectrum, Jul. 22, 2016, pp. 1-5, abstract only.

Ali, T. et al. "Anthocyanin-Loaded PEG-Gold Nanoparticles Enhanced the Neuroprotection of Anthocyanins in an $A\beta_{1-42}$ Mouse Model of Alzheimer's Disease" *Mol Neurobiol.*, 2017, pp. 6490-6506, vol. 54, No. 8.

NANOPARTICLES FOR USE FOR TREATING A NEURONAL DISORDER

CROSS-REFERENCE TO RELATED APPLICATION

This application is the U.S. national stage application of International Patent Application No. PCT/EP2018/085593, filed Dec. 18, 2018.

The present invention relates to the medical field, in particular to the treatment of neurological disorders. More specifically the present invention relates to a nanoparticle or nanoparticles' aggregate for use in prevention or treatment of a neurological disease or at least one symptom thereof in a subject without exposure of the nanoparticle or nanoparticles' aggregate to an electric field, and preferably without exposure thereof to any other external activation source such as a light source, a magnetic field, or an ultrasound source, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100. It further relates to compositions and kits comprising such nanoparticles and/or nanoparticles' aggregates as well as to uses thereof without exposure thereof to an electric field, and preferably without exposure thereof to any other external activation source such as a light source, a magnetic field, or an ultrasound source.

BACKGROUND

Neurological disorders are a major health concern (*Neurological disorders public health challenges*. WHO, 2006). Impairment of neural network function may have different origins. Parkinson's disease is a movement disorder caused by death of dopamine neurons in the substantia nigra, located in the midbrain. Stroke corresponds to a block in the brain's blood supply. Without oxygen, neurons in the affected area die, and the part of the body controlled by those cells cannot function. Huntington's disease is a genetic disorder. Epilepsy is a disorder caused by abnormal excitation of large groups of neurons in various brain regions. Alzheimer's disease is a neurodegenerative disorder characterized by the death of neurons in the hippocampus, cerebral cortex, and other brain regions. The causes of autism spectrum disorders are multifactorial: genetic, environmental, etc.

Neurological disorders can be classified depending on the primary symptoms that affect the patients. Three main types of symptoms are observed: motor disorders, psychiatric (mood/social) disorders and cognitive disorders as further explained herein below.

Motor disorders encompass tremor, hypokinesia such as bradykinesia or dyskinesia, muscle twisting, rigidity, postural instability, gait freezing, etc. Diseases presenting motor disorders include typically Parkinson's disease, dystonia, epilepsy, Huntington's disease and Tourette's syndrome.

Psychiatric disorders constitute a variety of diseases presenting symptoms of mood/social impairments. A non-exhaustive list includes autism spectrum disorders, schizophrenia disorders, bipolar disorders, depressive disorders, anxiety disorders, obsessive-compulsive disorders, substance-related and/or addictive disorders (*definition from the Diagnostic and Statistical Manual of Mental Disorders, 2013, fifth edition, the American Psychiatric Association*).

Some patients suffering of motor disorders, like Parkinson's disease and dystonia, can develop psychiatric disorders in the late stage of the diseases.

Cognitive disorders are present in many if not all mental disorders (e.g., schizophrenia, bipolar disorders). Only disorders whose core features are cognitive are included in the cognitive disorders category. Cognitive disorders affect the daily life of patients: simple tasks are complicated to achieve. Dementia is a representative cognitive disorder and it is a general term for a decline in mental ability severe enough to interfere with daily life. Alzheimer's disease is a peculiar type of dementia, with a neurodegenerative aspect.

Neurological disorders are, when possible, treated with drugs which play on regulation of the level of neurotransmitters in the brain and on control of interactions with their specific neurotransmitter receptors. The main neurotransmitters involved are: glutamate, γ-aminobutyric acid (GABA), dopamine and acetylcholine. Glutamate and GABA neurotransmitters are of peculiar interest because they play the principal role in increasing (Platt et al., *The Veterinary Journal*, 2007, 173, 278-286: *The role of glutamate in central nervous system health and disease—a review*) and in reducing neuronal excitability, respectively (Holmes et al., *Mental Retardation and Developmental Disabilities*, 1995, 1, 208-219: *Role of glutamate and GABA in the pathophysiology of epilepsy*). Dopamine is involved in several brain functions: control of movement via the basal ganglia (an improper level of dopamine in the basal ganglia results in uncontrolled movements), pleasure reward seeking behavior (disturbance may lead to dysfunctional addiction), cognition (disorders of dopamine in frontal lobes may lead to decline in neurocognitive functions), etc. (Alcaro et al., *Brain Res. Rev.*, 2007, 56(2), 283-321: *Behavioral functions of the mesolimbic dopaminergic system: an affective neuroethological perspective*). Acetylcholine is a neurotransmitter involved in learning and memory at the central nervous system level (Hasselmo et al., *Curr Opin Neurobiol*, 2006, 16(6), 710-715: *The role of acetylcholine in learning and memory*).

A common medication to alleviate the motor symptoms of Parkinson's disease is levodopa, which is transformed in dopamine in the brain and by this way helps in balancing the deficit in dopamine.

Levodopa is associated to carbidopa, which helps in avoiding the levodopa transformation in dopamine in all the body. One issue of the levodopa treatment is the "on-off" phenomenon, which results in phases of immobility and incapacity associated with depression alternating with jubilant thaws (Lees et al., *J Neurology Neurosurgery Psychiatry*, Special Supplement, 1989, 29-37: *The on-off phenomenon*). Non-responsiveness of the late-stage Parkinson's disease patients to this treatment is an issue (Fabbri et al., *Parkinsonism and related disorders*, 2016: *Do patients with late-stage Parkinson's disease still respond to levodopa?*). Other common medications to treat symptoms of neuropsychiatric disorders, like the "positive" symptoms, delusions and hallucinations, in schizophrenia are antipsychotic drugs.

However, therapeutic treatments of neurological disorders' symptoms with these drugs are non-specific, and as such, they may induce severe adverse events. In addition, refractoriness to the used drug may appear.

With advancing comprehension of neuroscience, brain can be thought as an electric network, coding and transmitting information through its electric wires, neurons. Connectivity between neurons is simple and complex at the same time: simple because it lies on influx/efflux of ions inside neurons, which result in action potentials (or "spikes"

of electric activity); complex because the brain network is composed of hundreds of billion neurons, which form nodes, hubs and modules that demonstrate coordinated interactions, at various spatial and temporal scales (Fornito et al., *Nature Reviews Neuroscience*, 2015, 16, 159-172: *The connectomics of brain disorders*). Neural communication depends on the anatomical components that connect individual neurons (structure) and on the process of transmitting information (function). Both aspects affect the overall performance of the nervous system. Neuronal interactions are traduced by oscillations of the brain electric activity pattern, which oscillations are measurable typically by electroencephalogram (EEG). Different frequency bands of oscillations are observed: delta, theta, alpha, beta, gamma (Ward et al., *Trends in Cognitive Sciences*, 2003, 7(12), 553-559: *Synchronous neural oscillations and cognitive processes*). Structurally, the most striking neuroanatomical feature of the brain is the abundant connectivity between neurons, which reflects the importance of neural communication. Synchronization of oscillations ("synchrony") between one brain area and another seems to constitute the last level of information coding [first level (neuron): action potentials; second level (neuronal network(s)): neuronal oscillations] by bringing spatio-temporal coordination (Engel et al., *Nature Reviews Neuroscience*, 2001, 2, 704-716: *Dynamic predictions: oscillations and synchrony in top-down processing*). Importantly, evidence is emerging that a delicately balanced pattern of synchronization and desynchronization in space and time is fundamental to the functional performance of the nervous system (Schnitzler et al., *Nature Reviews Neuroscience*, 2005, 6, 285-296: *Normal and pathological oscillatory communication in the brain*).

Abnormal synchronization processes (too high and/or too extended synchrony, i.e. also named hypersynchrony, or too low synchrony, i.e. also named impaired synchrony), have been associated with several brain disorders, such as epilepsy, schizophrenia, dementia and Parkinson's disease (Schnitzler et al., *Nature Reviews Neuroscience*, 2005, 6, 285-296: Normal and pathological oscillatory communication in the brain).

Nowadays, modulation of the electric activity pattern of neurons (neuromodulation) may be induced through electrical stimulations. The current techniques to produce an electric stimulus into the brain utilize either a direct electric stimulation or the induction of an electric field through the application of an electric current through a magnetic coil. Because certain neurological disorders affect areas in the deep brain and as the penetration depth of electric field is weak, the surgical implantation of electrodes inside the brain to continuously deliver electrical stimuli has been implemented and constitutes the "deep brain stimulation" (DBS) technique. Its efficacy depends on the parameters used for stimulation, especially the frequency. In 1987, high-frequency stimulation (≥100 Hz) of the ventralis intermedius (VIM) with implanted electrodes has been found to relieve the tremor symptoms for patients suffering from Parkinson's disease (Benabid et al., *Applied Neurophysiology*, 1987, 50, 344-346: *Combined (thalamotomy and stimulation) stereotactic surgery of the VIM thalamic nucleus for bilateral Parkinson disease*). Also, it has been shown in monkeys that high-frequency stimulation (>100 Hz), compared to low-frequency stimulation (<50 Hz), allows changes in the temporal firing pattern of neurons in the globus pallidus external (GPe) and the globus pallidus internal (GPi) (stimulus-synchronized regular firing pattern, which blocks transmission of altered patterns of neuronal activity in the basal ganglia to its target structures in the thalamus and the brainstem, thus alleviating the bradykinesia and rigidity symptoms (Hashimoto et al., *The Journal of Neuroscience*, 2003, 23(5), 1916-1923: *Stimulation of the subthalamic nucleus changes the firing pattern of pallidal neurons*). DBS is nowadays approved to treat several motor disorders (Parkinson's disease, dystonia, essential tremor, epilepsy) and psychiatric disorders (Obsessive Compulsive Disorder, depression).

However, several drawbacks may be associated to DBS, the first being the invasiveness of the technique and the risks of various complications like hemorrhage, epileptic seizures, infections, lead migration, lead breakage, etc. (Fenoy et al., *J Neurosurg*, 2014, 120, 132-139: *Risks of common complications in DBS surgery: management and avoidance*).

Focality (i.e. spatial resolution) of the generated electrical field in the target is another concern. The spread of electrical stimulus has also been linked to side-effects such as depression. A lot of research has been dedicated to design new types of electrodes which can shift and confine the stimulus within a certain area (Luan et al., *Frontiers in Neuroengineering*, 2014, 7(27), 1-9: *Neuromodulation: present and emerging methods*). Other technological aspects are under evaluation: the electrodes (or leads), their size, the invasiveness of the DBS device, the material constituting the leads, the compatibility with (magnetic resonance) imaging techniques, the battery life of the internal pulse generator (IPG) associated with the need for continuous stimulation.

The main others existing types of electrical stimulation, namely the transcranial electrical stimulation or transcranial magnetic stimulation, have the advantage not to be invasive, but the penetration depth of the electric field is weak. As such, their applications are limited to stimulation of the cerebral cortex (deep brain is not reachable). Moreover, the spatial resolution remains poor.

The present invention deals with nanoparticles and/or nanoparticles' aggregates (aggregates of nanoparticles) for use for preventing or treating/for use in prevention or treatment of a neurological disease (typically neuronal networks' disorders) or at least one symptom thereof.

The nanoparticles or nanoparticles' aggregates normalize the synchronization of neuronal oscillations (improve synchrony) within and/or between neuronal networks, and within and/or between distinct regions of the brain. Nanoparticles or nanoparticles' aggregates herein described by inventors thus help the subject/patient to return to a healthy/normal state.

The nanoparticles and aggregates of nanoparticles herein described by inventors do not require the application/induction of an electric current or field/stimulus, and preferably do not require exposure to any other external activation source such as a light source, a magnetic field, or an ultrasound source, to exert their function (i.e. to be efficient). The herein described nanoparticles and aggregates of nanoparticles do not require to be exposed to an electric current or field/stimulus, and preferably do not require to be exposed to any other external activation source such as a light source, a magnetic field, or an ultrasound source, to be functional in the context of the herein described uses. Inventors have discovered that these nanoparticles or aggregates of nanoparticles can advantageously and surprisingly be used efficiently without being exposed, or without exposure of the subject they are administered to, to an electric current or field/stimulus, typically to an electric current or field/stimulus applied to said subject for example by deep brain stimulation (DBS), by transcranial electric stimulation (TES), or by transcranial magnetic stimulation (TMS), and preferably without exposure to any other external activation source such as a light source, a magnetic field, or an ultrasound source. This means that the treated subject will not suffer the negative side effects of exposure to an electric current or field/stimulus or to any other external activation source such as a light source, a magnetic field, or an ultrasound source, thanks to the present invention.

As well known by the skilled person in the art, a nanoparticle has an elevated/high surface/volume ratio, typically approximately 35%-40% of atoms are localized at the surface of a 10 nm-nanoparticle compared with less than 20% for a nanoparticle having a size above 30 nm. This high surface/volume ratio is associated with a strong surface reactivity that is size-dependent. As a result, nanoparticles (especially those smaller than 20 nm) may exhibit novel properties compared with bulk materials. For instance, gold particles are known to be chemically inert and resistant to oxidation at a macroscopic scale, while gold particles having a size below 10 nm have a chemically active surface. The toxic mechanisms associated with the chemical destabilization of metallic nanoparticles might be (i) the direct release of metals in solutions (dissolution process), (ii) the catalytic properties of metallic nanoparticles, and (iii) the redox evolution of the nanoparticle's surface, which can oxidize proteins, generate reactive oxygen species (ROS) and induce an oxidative stress (cf. M. Auffan et al., *Environmental Pollution* 157 (2009) 1127-1133: *Chemical Stability of metallic nanoparticles: a parameter controlling their potential cellular toxicity in vitro*).

Beside herein above described gold nanoparticles which present catalytic properties, cerium oxide (7 nm-$CeO_2$ particle) or iron oxide (20 nm-$Fe_3O_4$ particle) nanoparticles have shown redox modification of their surface leading to cytotoxic effects related to an oxidative stress in vitro (cf. M Auffan et al., *Environmental Pollution* 157 (2009) 1127-1133: *Chemical Stability of metallic nanoparticles: a parameter controlling their potential cellular toxicity in vitro*). As well, 11 nm-silica nanostructure is eroded by biological media (cf. S-A Yang et al., Scientific Reports 2018 8:185: Silica nanoparticle stability in biological media revisited).

As herein below explained by inventors, nanoparticle having a size below 30 nm, are thus to be carefully selected when intended to be used in vivo in a subject, typically in a mammal, in particular in a human being.

BRIEF DESCRIPTION

Herein advantageously described for the first time is a nanoparticle or nanoparticles' aggregate for use for preventing or treating/for use in prevention or treatment of a neurological disease or at least one symptom thereof in a subject in need thereof without exposure of the nanoparticle or nanoparticles' aggregate to an electric field, and preferably without exposure thereof to any other external activation source such as a light source, a magnetic field, or an ultrasound source. The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

Inventors herein describe, in a particular aspect, a nanoparticle or nanoparticles' aggregate for use in prevention or treatment of a neurological disease or at least one symptom thereof in a subject without exposure of the nanoparticle or nanoparticles' aggregate to an electric field nor to any other external activation source, wherein the nanoparticle's or nanoparticles' aggregate's material is selected from a conductor material, a semiconductor material, an insulator material with a dielectric constant $\varepsilon_{ijk}$ equal to or above 200, and an insulator material with a dielectric constant $\varepsilon_{ijk}$ equal to or below 100, wherein i) the median largest size of the core of the nanoparticle or nanoparticles' aggregate of the population is of at least 30 nm when the material is a conductor material, a semiconductor material or an insulator material with a dielectric constant $\varepsilon_{ijk}$ equal to or above 200, and wherein ii) the core of the nanoparticle or nanoparticles' aggregate is coated with a biocompatible coating providing a neutral or a negative surface charge when measured in a solution of water having a concentration of electrolytes between 0.001 and 0.2 M, a concentration of the nanoparticles' or nanoparticles' aggregates' material between 0.01 and 10 g/L and a pH between 6 and 8.

Also herein described is the use of a nanoparticle or nanoparticles' aggregate for preparing a composition for preventing or treating a neurological disease as herein described or at least one symptom thereof in a subject in need thereof without exposure of the nanoparticle or nanoparticles' aggregate to an electric field, and preferably without exposure thereof to any other external activation source such as a light source, a magnetic field, or an ultrasound source.

Also herein described is a composition for use for preventing or treating/for use in prevention or treatment of a neurological disease or at least one symptom thereof in a subject, wherein the composition comprises, or consists of, nanoparticles and/or nanoparticles' aggregates and a pharmaceutically acceptable support, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100, and wherein the prevention or treatment is performed without exposure to an electric field of the nanoparticles or nanoparticles' aggregates administered to the subject through the composition, and preferably without exposure thereof to any other external activation source such as a light source, a magnetic field, or an ultrasound source.

Further herein described is a kit comprising, or consisting of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100, and uses thereof typically in prevention or treatment of/in a method for preventing or treating a neurological disease or at least one symptom thereof in a subject without exposure of the nanoparticles or nanoparticles' aggregates to an electric field, and preferably without exposure thereof to any other external activation source such as a light source, a magnetic field, or an ultrasound source.

DETAILED DESCRIPTION

The human nervous system is estimated to consist of roughly 80-120 billion nerve cells (Herculano-Houzel S. *Frontier in Human Neuroscience* (2009), 3(31): 1-11, *The human brain in numbers: a linearly scaled-up primate brain*). The defining characteristic of a neuron (or nerve cell) is its ability to transmit electrical signals in the form of action potentials.

The neuron/nerve cell constitutes the elementary node of the brain. Nerve cells can communicate with each other in a highly-structured manner forming neuronal networks. Neuron communicates via synaptic connections. Within neuron, nanocircuits constitute the underlying biochemical machinery for mediating key neuronal properties such as learning and memory and the genesis of neuronal rhythmicity. A microcircuit can be formed with just only a few interconnected neurons and can perform sophisticated tasks such as mediate reflexes, process sensory information, initiation of locomotion, and learning and memory mediation. A macrocircuit is a more complex network which consists of multiple imbedded microcircuits. Macrocircuits mediate higher brain functions such as object recognition and cognition. So, multiple levels of networks occupy the nervous system.

Neural Network Excitability

Neurons send messages electrochemically (i.e. chemicals/ions cause an electrical signal). The important ions in the nervous system are sodium and potassium, calcium and chloride. When a neuron is not sending a signal, it is "at rest." When a neuron is at rest, the inside of the neuron is negative relative to the outside. Although the concentrations of the different ions attempt to balance out on both sides of the membrane, they cannot because the cell membrane allows only some ions to pass through channels (ion channels). In addition to these selective ion channels, there is a pump that uses energy to move three sodium ions out of the neuron for every two potassium ions it puts in. Finally, when all these forces balance out, and the difference in the voltage between the inside and outside of the neuron is measured, the resting membrane potential (also "resting potential") of a neuron is about −70 mV. This means that the inside of the neuron is 70 mV less than the outside. At rest, there are relatively more sodium ions outside the neuron and more potassium ions inside that neuron. An action potential (also identified as "spike" or "impulse") occurs when a neuron sends information down an axon, away from the cell body. This means that some event (a stimulus) causes the resting potential to move toward 0 mV. When the depolarization reaches about −55 mV the neuron fires an action potential. If the depolarization does not reach this critical threshold level, then no action potential fires (on/off mechanism). Also, when the threshold level is reached, an action potential of fixed amplitude always fires. Therefore, either the depolarization does not reach the threshold or a full action potential is generated.

A great variability is found in the velocity of the propagation of action potentials. In fact, the propagation velocity of the action potentials in nerves can vary from 100 meters per second to less than a tenth of a meter per second. Whereas the time constant is an index of how rapidly a membrane will respond to a stimulus in time, the space constant (also length constant) is an index of how well an electric potential will spread along an axon as a function of distance.

Connectivity within and Between Neuronal Networks

There are three connectivity network types that are used to investigate communication within and across the brain. Structural connectivity is based on the detection of the fiber tracks that physically connect the regions of the brain. These are the anatomical network maps that indicate possible pathways that the signals can travel on in the brain. Functional connectivity identifies activity in brain regions that have similar frequency, phase and/or amplitude of correlated activity. Effective connectivity uses the functional connectivity information and goes one step further in determining the direct or indirect influence that one neural system may have over another, more specifically the direction of the dynamic information flow in the brain (Bowyer et al., *Neuropsychiatric Electrophysiology*, 2016, 2(1), 1-12: *Coherence a measure of the brain networks: past and present*).

The synchronized activity within a neuronal network can be detected by magnetoencephalogram (MEG), electroencephalogram (EEG), Functional Magnetic Resonance Imaging (FMRI) or Positron Emission Tomography (PET), then image using network connectivity analysis. MEG (Magnetoencephalogram) or EEG (Electroencephalogram) are preferred because they have high temporal resolution to resolve the dynamic flow of information. Connectivity analysis of the brain is performed to map out the communication networks needed for the brain to function. Specific regions in the brain are specialized for processing certain types of information. Imaging techniques have revealed that these regions are connected and communicate with other specialized regions across networks in the brain. "Coherence" (Bowyer et al., *Neuropsychiatric Electrophysiology*, 2016, 2(1), 1-12: *Coherence a measure of the brain networks: past and present*.) is a mathematical technique that quantifies the frequency and amplitude of the synchronicity (the state of being in synchrony or of being synchronized) of neuronal patterns of oscillating brain activity. Detection of the synchronous activation of neurons can be used to determine the wellbeing or integrity of the functional connectivity in the human brain. Overlaying the functional connectivity maps onto the structural connectivity images and the using direction of information flow derived from effective connectivity provides an all-inclusive understanding of how the brain functions. These techniques help to evaluate treatment therapies based on pre- and post-treatment brain connectivity imaging.

The intact (i.e. "normal" or "healthy") brain expresses complex patterns of ("normal" or "healthy") synchronous activity, associated with different 'states' of the organism, from slow delta rhythm (0.5-4 Hz), through theta (4-8 Hz), alpha (8-12 Hz), beta (15-30 Hz) and gamma (30-70 Hz) oscillations. Interestingly, the dissociated culture of cortical structures offers a convenient system for the examination of the rules that govern the emergence, generation and spread of network firing (spikes) and bursting (clusters of spikes) in populations of densely interconnected neurons. Network activity can be recorded for extended periods of time in a non-invasive manner and with finite time resolution using multielectrodes arrays. The 2-dimensional dissociated culture can be used as a viable test system for studying rules that govern the formation and maintenance of network activity in the brain, allowing the testing of hypothesis that cannot be addressed in the intact brain (Cohen E. et al., *Brain Research*, 2008, 1235, 21-30: *Determinants of spontaneous activity in networks of cultured hippocampus.*).

Herein advantageously described for the first time is a nanoparticle or nanoparticles' aggregate for use for preventing or treating/for use in prevention or treatment of a neurological disease or at least one symptom thereof in a subject in need thereof without exposure of the nanoparticle or nanoparticles' aggregate to an electric field, and preferably without exposure thereof to any other external activation source such as a light source, a magnetic field, or an ultrasound source. Such an exposure to a (therapeutic or diagnostic) electric field or to any other (therapeutic or diagnostic) external activation source such as a light source, a magnetic field or an ultrasound source are typically to be herein understood as being a therapeutic or diagnostic exposure, typically performed by medical staff, for example by a physician or a nurse.

The nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

The term "Treatment" refers to therapeutic treatment or measures able to prevent, alleviate or cure a disease, disorder or dysfunctional state as herein described. Such a treatment is intended for a mammal subject, preferably a human subject in need thereof. Are considered as such, the subjects already identified (diagnosed) as suffering from a disease, disorder or dysfunctional state as herein described, or those considered "at risk of developing" such a disease, disorder or dysfunctional state for whom the treatment is a preventive or prophylactic treatment.

In a particular aspect the subject is not a subject suffering of epilepsy.

Abnormal modulation of the oscillatory communication between neurons indeed exists in different types of neurological diseases or disorders (also herein identified as "neural diseases or disorders") (Uhlhaas et al., Neuron, 2006, 52, 155-168: *Neural synchrony in brain disorders: relevance for cognitive dysfunctions and pathophysiology*; Basar E. et al. *International Journal of Psychophysiology* 103 (2016) 135-148, *What does the broken brain say to the neuroscientist? Oscillations and connectivity in schizophrenia, Alzheimer's disease, and bipolar disorder*).

The human nervous system is divided into the central nervous system (CNS) and the peripheral nervous system (PNS). The CNS, in turn, is divided into the brain and the spinal cord, which lie in the cranial cavity of the skull and the vertebral canal, respectively. The CNS and the PNS, acting in concert, integrate sensory information and control motor and cognitive functions. FIG. 1 shows a simplified picture of the brain structure.

Synchrony (or synchronization) within and/or between neuronal networks, within and/or between distinct regions of the brain, is performed through the coordination of neuronal oscillations in time (Buzsaki et al., *Science*, 2004, 304, 1926-1929: Neuronal oscillations in cortical networks).

Motor disorders in a subject are typically due to hypersynchrony, which means that synchronization of oscillations within and/or between neuronal networks within and/or between distinct regions of the brain, typically observed on an electroencephalogram (EEG), is too high and/or too extended ("excessive") when compared to healthy/normal subject.

Psychiatric and cognitive disorders in a subject are typically due to an impaired synchrony, which means that synchronization of oscillations within and/or between neuronal networks within and/or between distinct regions of the brain, typically observed on an EEG, is lowered (typically presents a reduced activity) when compared to healthy/normal subject, or even disappears, i.e. is not detectable [cf. Table 1: Abnormal neural synchrony in neurological disorders (adapted from Uhlhaas et al., *Neuron*, 2006, 52, 155-168: *Neural synchrony in brain disorders: relevance for cognitive dysfunctions and pathophysiology*].

TABLE 1

| Type of symptoms | Neurological disorder | Neural synchrony |
|---|---|---|
| Motor | Parkinson's disease Epilepsy Dystonia | high/extended (excessive) |
| Psychiatric | Schizophrenia Autism | low/not detectable (impaired) |
| Cognitive | Alzheimer's disease | |

As "coherence" is a mathematical technique that quantifies the frequency and amplitude of the synchronicity in a subject (the state of being in synchrony or of being synchronized) of neuronal patterns of oscillating brain activity, it can be thought that a too high and a too low coherence when compared to healthy/normal subject are involved in motor disorders and psychiatric/cognitive disorders, respectively (Bowyer et al., *Neuropsychiatric Electrophysiology*, 2016, 2(1), 1-12: Coherence a measure of the brain networks: past and present) (cf. FIG. 2).

In a particular aspect, the neurological disease or disorder targeted in the context of the invention is selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, anxiety disorder, addiction disorder, consciousness vegetative state, for example selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, addiction disorder, consciousness vegetative state, and at least one symptom thereof.

As already explained herein above, neurological diseases or disorders can be classified depending on the primary symptoms that affect the patients which are motor disorders, psychiatric (mood/social) disorders and cognitive disorders as further detailed herein below.

Example of Motor Disorders

Parkinson's Disease

Parkinson's disease (PD) affects about 7 to 10 million people worldwide and it is characterized by tremor, dyskinesia, bradykinesia, gait freezing, etc. PD is a slowly progressive, degenerative disease of the brain. It affects nerve cells in the areas of the brain called the basal ganglia and the substantia nigra. Nerve cells in the substantia nigra produce dopamine, a neurotransmitter that acts as a chemical messenger in brain circuits important for planning and controlling body movement. In PD, the dopamine producing nerve cells of the substantia nigra die off prematurely in some individuals (Corti et al., *Physiol Rev*, 2011, 91, 1161-1218: *What genetics tells us about the causes and mechanisms of Parkinson's disease*). When dopamine receptors in the striatum are not adequately stimulated, parts of the basal ganglia are either under- or over-stimulated. In particular, the subthalamic nucleus (STN) becomes overactive and acts as an accelerator on the globus pallidus internus (GPi). The overstimulation of the GPi has an over-inhibitory effect on the thalamus, which in turn decreases its output and causes slowing of motion, and rigidity (Guo et al., *Frontiers in Computational Neuroscience*, 2013, 7, 124, 1-11: *Basal ganglia modulation of thalamocortical relay in Parkinson's disease and dystonia*).

The lack of dopamine in PD has been related to excessive oscillatory synchronization in the beta frequency throughout the cortical-basal ganglia motor network. Indeed, the dopamine levels in the basal ganglia are predicted to suppress beta synchrony, which in turn mediate the dopaminergic involvement necessary for movement anticipation (Jenkinson et al., *Trends in Neuroscience*, 2011, 34(12), 611-618: *New insights into the relationship between dopamine, beta oscillations and motor function*). If the level of dopamine in the basal ganglia is not high enough, then there is no control of beta oscillations synchrony anymore, and slowness of movements may appear. Another observation in parkinsonian patients leads to the conclusion that cortical oscillations in the beta band, lead and drive those in the basal ganglia (Lalo et al., *The Journal of Neuroscience*, 2008, 28(12), 3008-3016: *Patterns of bidirectional communication between cortex and basal ganglia during movement in patients with Parkinson disease*).

Deep Brain Stimulation (DBS) can be used to treat the symptoms of tremor and rigidity (Eusebio et al., *J Neurol Neurosurg Psychiatry*, 2011, 82, 569-573: *Deep brain stimulation can suppress pathological synchronization in parkinsonian patients*). The treatment of PD symptoms by DBS is FDA-approved since 2002 (essential tremor since 1997). The electrical stimulation is typically performed in basal ganglia, in the STN and in the GPi. As mentioned above, cortical beta-oscillations are also involved in the pathophysiology of the disease, so transcranial stimulation (such as transcranial magnetic stimulation—TMS) of the cortex could also be used to treat the Parkinson's disease symptoms (Cantello et al., *Brain Research Reviews*, 2002, 38, 309-327: *Transcranial magnetic stimulation and Parkinson's disease*).

Dystonia

Dystonia is a neurological disorder characterized by abnormal, involuntary twisting and turning movements that reflect impaired motor system function. Several forms of dystonia exist, depending on the part of the body affected by the symptoms, on their genetic origin, on the type of neurotransmitter involved, etc. The dystonic Central Nervous System (CNS) exhibits a deficient inhibition, which provokes the loss of reciprocal spinal inhibition between opposing muscles. In the case of upper dystonia for example, an abnormal synchronization of neurons/nerves giving the input signal to the forearm antagonist muscles leads to co-contraction of these antagonist muscles (dystonic symptom) (Farmer et al., *Brain*, 1998, 121, 801-814: *Abnormal motor unit synchronization of antagonist muscles underlies pathological co-contraction in upper limb dystonia*).

The DBS target point showing interesting antidystonic effect is the globus pallidus internus (GPi-DBS). GPi-DBS was approved by FDA in 2003 for patients with chronic, medically intractable dystonia (Hu et al., *Translational Neurodegeneration*, 2014, 3(2), 1-5: *Deep brain stimulation for dystonia*). Stimulation of the ventral intermediate (VIM) nucleus of the thalamus (VIM-DBS) produces much less robust effects. Stimulation using the subthalamic nucleus (STN-DBS) has been experimental. GPi-DBS provides relief of the main symptoms of dystonia, but it can take weeks to months for the therapeutic effects to fully develop (Dressler et al., *J Neural Transm*, 2015, DOI 10.1007/s00702-015-1453-x: *Strategies for treatment of dystonia*).

Epilepsy

Epilepsy is a brain disorder, which affects about 50 million people worldwide, and which is characterized predominantly by recurrent and unpredictable interruptions of normal brain function, called epileptic seizures. Epilepsy is not a singular disease entity but a variety of disorders reflecting underlying brain dysfunction that may result from many different causes (genetic mutation, brain tumors, head trauma, strokes, alcoholism, inflammation of the brain, infections such as meningitis, HIV or viral encephalitis, etc.) (Fisher et al., *Neurology*, 2015, 28(2), 130-135: *Redefining epilepsy*).

An epileptic seizure is defined as a transient occurrence of signs and/or symptoms due to excessive synchronous neuronal activity in the brain (Fisher et al., *Epilepsia*, 2005, 46(4), 470-472: *Epileptic seizures and epilepsy: definitions proposed by the International League Against Epilepsy (ILAE) and the International Bureau for Epilepsy (IBE)*). Cerebral cortex is the primary element in the generation of epileptic seizures: many people are diagnosed with focal frontal lobe or medial temporal lobe seizures (*National Institute of Neurological Disorders and Stroke*: see Worldwide website: ninds.nih.gov/disorders/epilepsy/detail_epilepsy.htm#3109_7). The identification of areas of elevated local synchrony, or "hypersynchrony", in the cortex suggests that local hypersynchrony may be a marker of seizure-generating areas (Schevon et al., *Neuroimage*, 2007, 35(1), 140-148: *Cortical abnormalities in epilepsy revealed by local EEG synchrony*).

Neurostimulation for treatment of epilepsy can take the form of peripheral nerve stimulation, such as vagus nerve stimulation (VNS); spinal cord stimulation; transcranial brain stimulation (TES or TMS); or deep brain stimulation (DBS). Responsive neurostimulation is another strategy, where stimulation is delivered only when seizure onset is detected. VNS and responsive neurostimulation have both been approved by the FDA for the treatment of certain types of epilepsy in the USA. DBS of the anterior nucleus of the thalamus (ANT) has been approved in countries of the European Union (Fisher et al., *Nature Reviews Neurology*, 2014, 10, 261-270: *Electrical brain stimulation for epilepsy*).

Examples of Psychiatric Disorders (Mood/Social Impairments)

Obsessive Compulsive Disorders (OCD)

Obsessive-compulsive disorder (OCD) is a common psychiatric disorder that is often chronic, severe, and extremely debilitating. It is also usually refractory to treatments, with a substantial proportion of patients failing to respond or obtaining only partial relief.

Functional neuroimaging studies have demonstrated dysfunction in the orbitofrontal cortex, basal ganglia and striatum.

A study has shown that acute OCD symptoms may be related to an abnormal high oscillatory activity in the subthalamic nucleus (STN), particularly in the left hemisphere and in the delta-alpha (1-12 Hz) frequency range (Bastin et al., *Cortex*, 2014, 60, 145-150: *Changes of oscillatory activity in the subthalamic nucleus during obsessive-compulsive disorder symptoms: two case reports*). Furthermore, some subthalamic neurons specifically increased their firing rate when doubt occurred during a verification task (Burbaud et al., *brain*, 2013, 136(1), 304-317: *Neuronal activity correlated with checking behavior in the subthalamic nucleus of patients with obsessive-compulsive disorder*).

DBS of the ventral anterior limb of the internal capsule (VC) and adjacent ventral striatum (VS) was approved in the EU for the treatment of severe and highly resistant-treatment OCD (VC/VS-DBS).

Autism Spectrum Disorders

Autism is a neurodevelopmental syndrome that is defined by deficits in social reciprocity and communication, and by unusual restricted, repetitive behaviors. Autism is a disorder that usually begins in infancy, at the latest, in the first three years of life. Autism is a heterogeneous condition (no two children or adults with autism have similar profile), which has led to the concept of "autism spectrum disorder", classifying several levels of the disease according to the degree of language deficit or general cognitive delay, and according to the severity of social or behavioral symptoms (Lord et al., Neuron, 2000, 28, 355-363: *Autism spectrum disorders*). At one end of this spectrum, individuals with autism are high functioning, enabling them to live on their own and maintain employment. Individuals characterized as low functioning exhibit more severe symptoms: difficulties for language (or even nonverbal language), poor social communication, self-injurious behavior (SIB), tantrums, and aggression that can be potentially life threatening. An important trend in structural and functional studies of the brain in autism is the involvement of the network for socioemotional processing: the limbic system, the facial processing system and the mirror neuron network. A deficit in synchronization of gamma-band oscillations has been shown to be involved in the apparition of symptoms (Sinha et al., *Neurosurgery Focus*, 2015, 38(6), E3: *Deep brain stimulation for severe autism: from pathophysiology to procedure*).

Two major symptom domains that may require treatment in severe autism are social deficits, including being nonverbal and nonresponsive to speech, and SIB, which can be life threatening. The amygdala seems to play an important role in the pathophysiology of these abnormalities. Altered excitatory or inhibitory control is implicated in the abnormality of autism pathophysiology. Neuromodulation of amygdalar targets via DBS may represent a therapeutic intervention for patients with severe autism. Three cases of DBS treatment were reported in literature. The aim of treatments was mainly to alleviate motor disorders like the stereotypies (repeated movement pattern) and the self-injurious behaviors (SIB) associated to the disease (Sinha et al., *Neurosurgery Focus*, 2015, 38(6), E3: *Deep brain stimulation for severe autism: from pathophysiology to procedure*; Stocco et al., *Parkinsonism and related disorders*, 2014, 20, 1035-1036: *Deep brain stimulation for severe secondary stereotypies*). In one of the three cases, it was reported that DBS in the basolateral nucleus resulted in a significant improvement in autism-related symptoms like social contact, affect modulation and nocturnal sleep (Sturm et al., *Frontiers in Human Neuroscience*, 2013, 6, 341, 1-10).

Schizophrenia

Schizophrenia is a chronic psychiatric illness characterized among others by the following symptoms: positive symptoms, which reflect aberrant mental activity (hallucinations and delusions); negative symptoms, which correspond to the deficiency of a mental function which is normally present (thought disorder, blunting of affect, poverty of speech). Regarding the causes of disability in the lifespan, schizophrenia is located within the top ten.

Prominent ventricular enlargement and increased cerebrospinal fluid on the brain surface suggest that the brain has atrophied. This loss of gray matter and the reduced numbers of synaptic structures on neurons suggest that schizophrenia is a neurodevelopmental disorder, which means that brain abnormalities are already present in first-episode patients (in contrast to neurodegenerative disorder). In schizophrenia patients, the observed impaired neural circuitry has been demonstrated to be due to a failure of gamma-band synchronization (Spencer et al., *The Journal of Neuroscience*, 2003, 23(19), 7407-7411: *Abnormal neural synchrony in schizophrenia*; Gallinat et al., *Clinical Neurophysiology*, 2004, 115, 1863-1874: *Reduced oscillatory gamma-band responses in unmedicated schizophrenic patients indicate impaired frontal network processing*).

Electroconvulsive therapy (ECT), i.e. shock treatment, has been demonstrated to be one of the most successful non-pharmacological treatments in schizophrenia (Payne et al., *J. Psychiatr. Pract.*, 2009, 15(5), 346-368: *Electroconvulsive therapy part I: a perspective on the evolution and current practice of ECT*). It involves the successive application of electrical current to the brain, which provokes seizures comparable to epileptic ones.

Electric stimulation for the symptomatic treatment of schizophrenia is also possible through DBS. For example, DBS of the nucleus accumbens (NAcc) in depression leads to remission of anhedonia, i.e. recovery of hedonic pleasure (Schlaepfer et al., *Neuropsychopharmacology*, 2008, 33, 368-377: *Deep brain stimulation to reward circuitry alleviates anhedonia in refractory major depression*).

Example of Cognitive Disorder

Alzheimer's Disease

Alzheimer's disease (AD) is a neurodegenerative disorder and it leads to progressive loss of mental, behavioral, functional decline and ability to learn. As of 2013, an estimated 5.2 million Americans had AD with approximately 200 000 people younger than 65 years and 5 million aged 65 years or older (*Alzheimers Dement.* 2013, 9(2), 208-245: 2013 *Alzheimer's disease facts and figures*). Recent evidence indicates that cognitive deficits seen in Alzheimer's disease are associated with a functional disconnection of neuro-cognitive networks. Analyses of global EEG synchronization reveal a widespread reduction in the alpha-, beta- and gamma-band synchronization, concomitant with an increase in the delta-band synchronization. In patients with mild Alzheimer's disease, a loss of beta-band synchronization has been shown to correlate with cognitive impairment (Schnitzler et al., *Nature Reviews Neuroscience*, 2005, 6, 285-296: *Normal and pathological oscillatory communication in the brain*). Clinical investigations are ongoing to evaluate the potential of DBS for the treatment of Alzheimer's disease.

Nanoparticles

Herein described is a nanoparticle or aggregate of nanoparticles for use according to the invention for preventing or treating/for use in prevention or treatment of a neurological disease or at least one symptom thereof in a subject without exposure of the nanoparticle or aggregate of nanoparticles to an electric field, and preferably without exposure of said nanoparticle or aggregate of nanoparticles to any other external activation source such as a light source, a magnetic field, or an ultrasound source, wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100.

The Nanoparticle's or Nanoparticles Aggregate's Dimension or Size

In the spirit of the invention, the terms "nanoparticle" or "nanoparticles' aggregate" refers to a product, in particular a synthetic product, with a size in the nanometer range, typically between 1 nm and 1000 nm, or between 1 nm and 500 nm, for example between at least 10 nm and about 500 nm or about 1000 nm, between at least 30 nm and about 500 nm or about 1000 nm, between at least 40 nm and about 500 nm or about 1000 nm, between at least 45 nm and about 500 nm or about 1000 nm, preferably below 500 nm.

The term "aggregate of nanoparticles" or "nanoparticles' aggregate" refers to an assemblage of nanoparticles strongly, typically covalently, bound to each other.

Electron microscopy such as Scanning Electron Microscopy (SEM), Transmission electron microscopy (TEM), or cryo-TEM, can be used to measure the size of the nanoparticle or of the aggregate of nanoparticles, and more particularly the size of the core of the nanoparticle or nanoparticles' aggregate, i.e., the nanoparticle or nanoparticles' aggregate without its biocompatible coating. As a matter of fact, the biocompatible coating is generally made of compounds which consist mainly of light elements (polymer or organic compounds), whose elastic interactions with the energetic electrons are relatively weak, resulting in a poor image contrast. The TEM measures the projected images of particles deposited onto an electron-transparent substrate. The recording of more than about 50, preferably more than about 100, 150 or 200 nanoparticles or nanoparticles' aggregates per sample should typically be measured for size assessment. The recording of more than about 50, or preferably more than about 100, 150 or 200 nanoparticles or nanoparticles' aggregates therefore allows for establishing the median largest size of the core of the nanoparticles or nanoparticles' aggregates of the population, as well as the size of the core of the nanoparticles or nanoparticles' aggregates representing the 30%-70% percentile of the population of nanoparticles and nanoparticles' aggregates. A typical assay protocol may be found in "NIST-NCL Joint Assay Protocol, PCC-7; Measuring the size of using transmission electron microscopy (TEM); version 1.1 December 2009".

As well, dynamic light scattering (DLS) can be used to measure the hydrodynamic diameter of nanoparticles or nanoparticles' aggregates (i.e., the diameter of the nanoparticle or of the nanoparticles' aggregate including both its core and its biocompatible coating) in solution. The hydrodynamic diameter is the diameter of an equivalent hard sphere that diffuses at the same rate as the analyte. A typical assay protocol may be found in "NIST-NCL Joint Assay Protocol, PCC-1; Measuring the size of nanoparticles in aqueous media using batch-mode dynamic light scattering; version 1.1 February 2010". Particle size results obtained from DLS measurement may not coincide with those obtained from other techniques (e.g. electron microscopy). This is due in part to differences in the physical property that is actually measured (e.g. hydrodynamic diffusion versus projected area). Moreover, DLS is sensitive to the presence of small quantities of large particles or of clusters of smaller particles, whereas electron microscopy typically reflects the size of primary particles (i.e. the size of the core of the nanoparticles or nanoparticles' aggregates) (cf. NIST-NCL Joint Assay Protocol, PCC-1; Measuring the size of nanoparticles in aqueous media using batch-mode dynamic light scattering; version 1.1 February 2010).

These two methods, DLS and electron microscopy, may further be used one after each other to compare size measures and confirm said size. A preferred method for measuring nanoparticles and nanoparticles' aggregates size is DLS (Ref. *International Standard ISO22412 Particle Size Analysis-Dynamic Light Scattering, International Organisation for Standardisation* (*ISO*) 2008). The mean hydrodynamic diameter of the nanoparticle or the aggregate of nanoparticles measured by DLS in solution is presented as size distribution by intensity (light scattering intensity is proportional to particle size) and measured at room temperature (about 25° C.).

Typically, the largest dimension or size is the diameter of a nanoparticle of round or spherical shape, or the longest length of a nanoparticle of ovoid or oval shape.

The largest dimension of a nanoparticle or aggregate as herein defined is typically between about 2 nm and about 250 nm or about 500 nm, preferably between about 4 nm or 10 nm and about 100 nm or about 200 nm, even more preferably between about (preferably at least) 10 nm and about 150 nm, between about (preferably at least) 30 nm and about 150 nm, between about (preferably at least) 40 nm and about 500 nm, between about (preferably at least) 45 nm and about 500 nm, preferably below 500 nm.

When the mean hydrodynamic diameter of the nanoparticle or the aggregate of nanoparticles in solution is measured, the DLS technique is typically used. Using DLS, the mean hydrodynamic diameter of the nanoparticle or the aggregate of nanoparticles in solution is typically between about 10 nm and about 500 nm, preferably between about 10 nm or about 30 nm and about 100 nm or about 500 nm, even more preferably between about 10 nm or about 30 nm and about 100 nm, about 150 nm, about 200 nm, about 250 nm, about 300 nm, about 350 nm, about 400 nm, about 450 nm, or about 500 nm.

When the core of the nanoparticle or nanoparticles' aggregate is measured, the electron microscopy technique is typically used. Using electron microscopy, the median largest size (also herein identified as "median largest dimension") of the core of the nanoparticle or of the nanoparticles' aggregate of the population is typically between about 5 nm and about 250 nm or about 500 nm, preferably between about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm or about 45 nm and about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 121 nm, about 122 nm, about 123 nm, about 124 nm, about 125 nm, about 130 nm, about 140 nm, about 150 nm, about 200 nm, about 250 nm, about 300 nm, about 350 nm, about 400 nm, about 450 nm or about 500 nm.

Typically, when measuring the size of the core of the nanoparticle or nanoparticles' aggregate with electron microscopy tools, the size of the core of the nanoparticle or nanoparticles' aggregate representing the 30%-70% percentile of the population of nanoparticles and nanoparticles' aggregates is comprised between about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 21 nm, about 22 nm, about 23 nm, about 24 nm, about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm or about 45 nm and about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, about 100 nm, about 101 nm, about 102 nm, about 103 nm, about 104 nm, about 105 nm, about 106 nm, about 107 nm, about 108 nm, about 109 nm, about 110 nm, about 111 nm, about 112 nm, about 113 nm, about 114 nm, about 115 nm, about 116 nm, about 117 nm, about 118 nm, about 119 nm, about 120 nm, about 121 nm, about 122 nm, about 123 nm, about 124 nm, about 125 nm, about 130 nm, about 140 nm, about 150 nm, about 200 nm, about 250 nm, about 300 nm, about 350 nm, about 400 nm, about 450 nm, about 500 nm or about 520 nm.

Composition of Nanoparticles

Nanoparticle Prepared from a Conductor Material

The nanoparticle prepared from a conductor material is an organic nanoparticle or an inorganic nanoparticle.

Inorganic nanoparticle prepared from a conductor material is typically prepared with a metallic element having a standard reduction potential E° value equal to or above about 0.01, typically when measured at 25° C. and at a pressure of 1 atm in respect to the standard hydrogen electrode (see Table 2 "reduction reactions having E° values more positive than that of the standard hydrogen electrode", 8-25, Handbook of chemistry and physics; David R. Lide; 88$^{th}$ Edition), more preferably equal to or above about 0.1, 0.2, 0.3, 0.4, or 0.5. Typical metallic elements used to prepare the nanoparticles may be selected from Tl, Po, Ag, Pd, Ir, Pt, Au, and a mixture thereof. Preferably, the metallic element usable as conductor material to prepare the nanoparticles is selected from Ir, Pd, Pt, Au, and a mixture thereof, even more preferably is selected from Au, Pt, Pd and any mixture thereof. Particularly preferred materials are Au and Pt.

Typically, gold nanoparticles have shown catalytic activity when their size was decreased to few nm (cf. M. Auffan et al., Nature Nanotechnology 2009, 4(10), 634-641: Towards a definition of inorganic nanoparticles from an environmental, health and safety perspective). In order to reduce the surface/volume ratio and thus minimize the contribution of the inorganic nanoparticle's surface to the catalytic activity, a median largest size of the core of the nanoparticle or of the nanoparticles' aggregate of the population of at least 30 nm, typically of at least 40 nm or at least 45 nm is preferred. Interestingly, inventors have discovered that gold nanoparticles with a median largest size of the core of the nanoparticle or of the nanoparticles' aggregate of the population equal to 45 nm and/or a size of the core of the nanoparticle or nanoparticles' aggregate representing the 30%-70% percentile of the population of nanoparticles and nanoparticles' aggregates between 42 nm and 49 nm, were more efficient to prevent/rescue MPP induced functional effects on the neuronal network than gold nanoparticles with a median largest size of the core of the nanoparticle of the population equal to 15 nm and/or a size of the core of the nanoparticle or nanoparticles' aggregate representing the 30%-70% percentile of the population of nanoparticles and nanoparticles' aggregates between 14 nm and 16 nm, the tested gold nanoparticles containing the same gold concentration (cf. examples 9 and 10).

Organic nanoparticle prepared from a conductor material is typically prepared with an organic material having contiguous sp2 hybridized carbon centers in its structure (i.e. carbon double bond or aromatic cycles comprising heteroatoms, typically N or S, within the aromatic cycle or outside the aromatic cycle). Preferred organic materials are selected from polyaniline, polypyrrole, polyacetylene, polythiophene, polycarbazole, polypyrene, poly(3,4-ethylenedioxythiophene) and/or poly(3,4-ethylenedioxythiophene) polystyrene sulfonate.

In a particular aspect, the median largest size of the core of the nanoparticle or nanoparticles' aggregate of the population is of at least 30 nm or of at least 40 nm and preferably below 500 nm as described herein above, for example of 45 nm, when the material is a conductor material as described herein above, in particular a metallic material, typically a metal having a standard reduction potential E° above 0.2, or an organic material, typically an organic material having contiguous sp2 hybridized carbon centers in its structure, preferably a metallic material as described herein above, in particular any one of Au, Pt, Pd and any mixture thereof.

Nanoparticle Prepared from a Semiconductor Material

The nanoparticle prepared from a semiconductor material is typically an inorganic nanoparticle. Inorganic nanoparticles are typically prepared with a semiconductor material presenting a relatively small energy band gap (Eg) between its valence and conduction bands. Typically, the semiconductor material has a band gap Eg below 3.0 eV, typically when measured at room temperature (about 25° C.) (see for instance table 12-77, Table 3; Handbook of chemistry and physics; David R. Lide; 88$^{th}$ Edition). In a particular aspect, the material is an intrinsic semiconductor material or an extrinsic semiconductor material as further herein described below.

Intrinsic semiconductor materials typically consist of an element from group IV A of the Mendeleev's periodic table, such as Silicon (Si) or Germanium (Ge), in a mixed composition of elements from groups III and V of the Mendeleev's periodic table, such as AlSb, AlN, GaP, GaN, InP, InN, etc., or in a mixed composition of elements from groups II and VI of the Mendeleev's periodic table, such as ZnSe, ZnTe, CdTe, etc.

Extrinsic semiconductor materials typically comprise, or consist of, an intrinsic semiconductor prepared with a high degree of chemical purity, wherein the intrinsic semiconductor material comprises a dopant. In a particular aspect, when the nanoparticle's or nanoparticles' aggregate's extrinsic semiconductor material consists of an element from group IVA of the Mendeleev's periodic table, it is doped with a charge carrier selected from Al, B, Ga, In and P. Such extrinsic semiconductor materials may be either of n-type in which negative charge carriers dominate or of p-type in which positive charge carriers dominate. Typical extrinsic p-type semiconductor material consists of silicon (Si) or germanium (Ge) doped with a charged carrier selected from aluminum (Al), Boron (B), Gallium (Ga) and indium (In); Typical extrinsic p-type semiconductor material consists of silicon (Si) or germanium (Ge) typically doped with phosphorus (P).

Typically, the band gap energy of semiconductor nanoparticles was shown to increase when the size of the nanoparticles decreased below 10 nm (cf. M. Auffan et al., Nature Nanotechnology 2009, 4(10), 634-641: Towards a definition of inorganic nanoparticles from an environmental, health and safety perspective). In order to ensure a low surface/volume ratio and maintain a bulk band gap of the nanoparticles or nanoparticles' aggregates below 3.0 eV, a median largest size of the core of the nanoparticle or the nanoparticles' aggregate of the population of at least 30 nm, preferably of at least 40 nm, is preferred.

Thus, in a particular aspect, the median largest size of the core of the nanoparticle or nanoparticles' aggregate of the population is of at least 30 nm or of at least 40 nm and preferably below 500 nm, when the material is a semiconductor material as described herein above, in particular a semiconductor material with a band gap Eg below 3.0 eV, typically a material consisting of an element from group IVA of the Mendeleev's periodic table, in particular an element from group IVA of the Mendeleev's periodic table doped with a charge carrier selected from Al, B, Ga, In and P, or of a mixed composition of elements from group III and V of the Mendeleev's periodic table, or of a mixed composition of elements from group II and VI of the Mendeleev's periodic table.

Nanoparticle Prepared from an Insulator Material Having a High Relative Dielectric Constant (Relative Permittivity), i.e. Equal to or Above 200

The nanoparticles prepared from, or consisting of, an insulator material having a high relative dielectric constant $\varepsilon_{ijk}$ (also named relative permittivity), are typically prepared with a material having a band gap Eg equal to or above 3.0 eV typically when measured at room temperature (about 25° C.) and a relative dielectric constant $\varepsilon_{ijk}$ equal to or above 200, which is typically measured between 20° C. and 30° C. and between $10^2$ Hz up to the infrared frequency (see for instance table 12-45 "Permittivity (dielectric constant) of inorganic solid"; *Handbook of chemistry and physics*; David R. Lide; 88th Edition; Compilation of the static dielectric constant of inorganic solid. K. F. Young and H. P. R. Frederikse. *J. Phys. Chem. Ref Data*, Vol. 2, No. 2, 1973).

Such nanoparticles are typically prepared with a dielectric material which is a mixed-metal oxide preferably selected from $BaTiO_3$, $PbTiO_3$, $KTaNbO_3$, $KTaO_3$, $SrTiO_3$, $BaSrTiO_3$, etc.

Typically, the perovskite-based structure $PbTiO_3$ nanoparticles have shown a change of their paraelectric-to-ferroelectric transition temperature for nanoparticles sizes less than 20 nm-30 nm (cf. M. Auffan et al., *Nature Nanotechnology* 2009, 4(10), 634-641: *Towards a definition of inorganic nanoparticles from an environmental, health and safety perspective*). In order to ensure a low surface/volume ratio and maintain the dielectric properties of the nanoparticles or nanoparticles' aggregates, a median largest size of the core of the nanoparticle or the nanoparticles' aggregate of the population of at least 30 nm, typically of at least 40 nm, is preferred.

Thus, in a particular aspect, the median largest size of the core of the nanoparticle or nanoparticles' aggregate of the population is of at least 30 nm or of at least 40 nm and preferably below 500 nm, when the material is an insulator material as described herein above having a high relative dielectric constant $\varepsilon_{ijk}$ equal to or above 200, in particular an insulator material with a band gap Eg equal to or above 3.0 eV, preferably a mixed-metal oxide selected from $BaTiO_3$, $KTaNbO_3$, $KTaO_3$, $SrTiO_3$ and $BaSrTiO_3$.

Nanoparticle Prepared from an Insulator Material Having a Low Relative Dielectric Constant (Relative Permittivity), i.e. Equal to or Below 100

The nanoparticles prepared from, or consisting of, an insulator material having a low relative dielectric constant are typically prepared with a material having a band gap Eg equal to or above 3.0 eV typically when measured at room temperature (about 25° C.) and a relative dielectric constant $\varepsilon_{ijk}$ equal to or below 100, preferably below 50 or below 20, which is typically measured between 20° C. and 30° C. and between $10^2$ Hz up to the infrared frequency, (see for instance table 12-45 "Permittivity (dielectric constant) of inorganic solid"; *Handbook of chemistry and physics*; David R. Lide; 88th Edition; Compilation of the static dielectric constant of inorganic solid. K. F. Young and H. P. R. Frederikse. *J. Phys. Chem. Ref Data*, Vol. 2, No. 2, 1973).

Such nanoparticles are typically prepared with a dielectric material which is selected from a metal oxide, a mixed metal oxide, the metallic element of which is from period 3, 5 or 6 of the Mendeleev's periodic table or a lanthanide, and a carbon material. The dielectric material is preferably selected from $Al_2O_3$, $LaAlO_3$, $La_2O_3$, $SiO_2$, $SnO_2$, $Ta_2O_5$, $ReO_2$, $ZrO_2$, $HfO_2$ and carbon diamond. More preferably, the dielectric material is a metal oxide selected from $ReO_2$, $ZrO_2$, $HfO_2$ and any mixture thereof. Particularly preferred is a dielectric material selected from $ZrO_2$ and $HfO_2$. In a particular and preferred aspect, the dielectric material or metal oxide is not $CeO_2$ (cerium oxide), $Fe_3O_4$ (iron oxide), $SiO_2$ (silica) or any mixture thereof.

Zirconium (Zr) and hafnium (Hf) are both elements in a $4^+$ oxidation state and, $Zr^{4+}$ and $Hf^{4+}$ elements are nearly identical in size and in chemical properties; this is the reason why, these two ions are considered together when establishing their aqueous chemistry (see chapter 8, section 8.2 Zr4+ and Hf4+, p. 147 "The hydrolysis of cations", Bass C. F. & Mesmer R. E.; John Wiley and Sons, Inc. reprint Edition 1986).

In a particular aspect, the median largest size of the core of the nanoparticle or nanoparticles' aggregate of the population is of at least 10 nm and preferably below 500 nm as described herein above, when the material is selected from $ReO_2$, $ZrO_2$, $HfO_2$, preferably from $ZrO_2$ and $HfO_2$, and any mixture thereof, as described herein above.

The Nanoparticle's or Nanoparticles Aggregate's Shape

As the shape of the particle or aggregate can influence its "biocompatibility", particle or aggregate having a quite homogeneous shape is preferred. For pharmacokinetic reasons, nanoparticles or aggregates being essentially spherical, round or ovoid in shape are thus preferred. Such a shape also favors the nanoparticle's or aggregate's interaction with cells or uptake by cells. Spherical or round shape is particularly preferred.

The shape of the nanoparticle or aggregate of nanoparticles is typically evaluated using electron microscopy such as transmission electron microscopy (TEM).

The Nanoparticles' or Aggregates of Nanoparticles' Biocompatible Coating

In a preferred embodiment, the core of the nanoparticle or nanoparticles' aggregate used in the context of the present invention to prepare a composition of interest can be coated with a biocompatible material selected from an agent exhibiting stealth property. Agent exhibiting stealth properties may be an agent displaying a steric group. Such a group may be selected for example from polyacrylate; polyacrylamide (poly(N-isopropylacrylamide)); polycarbamide; a biopolymer; a polysaccharide such as dextran or xylan; and collagen. In another preferred embodiment, the core of the nanoparticles or nanoparticles' aggregates can be coated with a biocompatible material selected from an agent allowing interaction with a biological target. Such an agent can typically bring a positive or a negative charge on the nanoparticle's or nanoparticles' aggregate's surface. An agent forming a positive charge on the nanoparticle's or nanoparticles' aggregate's surface can be for example aminopropyltriethoxisilane or polylysine. An agent forming a negative charge on the nanoparticle's or nanoparticles' aggregate's surface can be for example a phosphate (for example a polyphosphate, a metaphosphate, a pyrophosphate, etc.), a carboxylate (for example citrate or dicarboxylic acid, in particular succinic acid) or a sulphate.

In a preferred embodiment, the core of the nanoparticle or aggregate of nanoparticles used in the context of the present invention presents a hydrophilic neutral surface charge or is coated with a biocompatible material (i.e. a coating agent) selected from a hydrophilic agent conferring a neutral surface charge to the nanoparticle. Indeed, when the nanoparticles of the present invention are administered to a subject, nanoparticles presenting a hydrophilic neutral surface charge or the core of the nanoparticles coated with a biocompatible agent selected from a hydrophilic agent conferring a neutral surface charge to the nanoparticles are particularly advantageous to optimize the use of the herein described nanoparticles for treating a neurological disease.

A hydrophilic agent conferring neutral surface charge to the core of the nanoparticle or nanoparticles' aggregate may be an agent displaying a functional group selected from an alcohol (R—OH), an aldehyde (R—COH), a ketone (R—CO—R), an ester (R—COOR), an acid (R—COOH), a thiol (R—SH), a saccharide (glucose, fructose, ribose for instance), an anhydride (RCOOOC—R), and a pyrrole. The hydrophilic agent conferring a neutral surface charge to the core of the nanoparticle or nanoparticles' aggregate can be a monomer, a dimer, an oligomer, a polymer or a copolymer. When the agent is an oligomer, it may be an oligosaccharide such as a cyclodextrin. When the agent is a polymer, it may be a polyester (such as a poly(lactic acid) or a polyhydroxyalkanoic acid), a polyether, a polyethylene oxide, a polyethylene glycol, a polyvinylalcohol, a polycaprolactone, a polyvinylpyrrolidone, a polysaccharide such as a cellulose, a polypyrrole, etc.

In addition, a hydrophilic agent conferring neutral surface charge to the core of the nanoparticle or nanoparticles' aggregate may be an agent displaying specific groups (R—) able to interact with the surface of the nanoparticle or aggregate of nanoparticles. R is typically selected from a thiol, a silane, a carboxylic and a phosphate group.

When the core of the nanoparticle or aggregate of nanoparticles is a conductor or a semiconductor and a metallic nanoparticle, R is preferably a thiol, a thioether, a thioester, a dithiolane or a carboxylic group. Preferably, the hydrophilic neutral coating agent is selected from a thioglucose, a 2-mercaptoethanol, a 1-thioglycerol, a thiodiglycol and a hydroxybutyric acid.

When the core of the nanoparticle or aggregate of nanoparticles is an insulator, and an oxide or a mixed-oxide nanoparticle, R is preferably a silane or a phosphate group. Preferably, the hydrophilic neutral coating agent is a hydroxymethyltriethoxysilane, a fructose 6-phosphate or a glucose 6-phosphate compound.

A hydrophilic agent conferring neutral surface charge to the core of the nanoparticle or nanoparticles' aggregate may be a zwitterionic compound such as an amino acid, a peptide, a polypeptide, a vitamin or a phospholipid.

The surface charge of a nanoparticle or nanoparticles' aggregate is typically determined, as well known by the skilled person, by zeta potential measurements, typically in (a solution of) water having a concentration of nanoparticles' or nanoparticles' aggregates' material between 0.01 and 10 g/L, a pH between 6 and 8, and typically a concentration of electrolytes (in water) between 0.001 and 0.2 M, for example 0.01 M or 0.15 M. Under the herein above defined conditions, the surface charge of the nanoparticle or aggregate of nanoparticles is typically comprised between −10 mV and +10 mV (corresponding to a neutral surface charge), between −20 mV and +20 mV, or between −35 mV and +35 mV. When neutral, the surface charge of the nanoparticles or aggregate of nanoparticles is typically comprised between −10 mV, −9 mV, −8 mV, −7 mV, −6 mV, −5 mV, −4 mV, −3 mV, −2 mV, or −1 mV and 1 mV, 2 mV, 3 mV, 4 mV, 5 mV, 6 mV, 7 mV, 8 mV, 9 mV or 10 mV. When negative, the surface charge of the nanoparticles or aggregate of nanoparticles is typically below −11 mV, −12 mV, −13 mV, −14 mV −15 mV, −16 mV, −17 mV, −18 mV, −19 mV, −20 mV, −21 mV, −22 mV, −23 mV, −24 mV, −25 mV, −26 mV, −27 mV, −28 mV, −29 mV, −30 mV, −31 mV, −32 mV, −33 mV, −34 mV or −35 mV.

A full biocompatible coating of the nanoparticle or aggregate may be advantageous in the context of the present invention in order to avoid any electrical charge on the nanoparticle's surface, when the nanoparticle presents a hydrophilic neutral surface charge. The "full coating" implies the presence of a very high density/compactness of biocompatible molecules able to create at least a complete monolayer on the surface of the particle.

The biocompatible coating allows in particular the nanoparticle's stability in a fluid, such as a physiological fluid (blood, plasma, serum, etc.) or any isotonic media or physiologic medium required for a pharmaceutical administration.

Stability may be confirmed by dry extract quantification using a drying oven and measured on a nanoparticle suspension prior and after filtration, typically on a 0.45 μm filter.

Advantageously, the coating preserves the integrity of the particle in vivo, ensures or improves the biocompatibility thereof, and facilitates an optional functionalization thereof (for example with spacer molecules, biocompatible polymers, targeting agents, proteins, etc.).

The biocompatible nanoparticle or aggregate of nanoparticles of the invention should neither dissolve and release toxic species following in vivo administration (i.e. at physiological pH) nor present redox behavior, typically for said nanoparticle or aggregate of nanoparticles to be considered biocompatible, i.e. to be safely used in a subject, in particular in a mammal, preferably in a human being.

Another particular object herein described relates to a composition, in particular a pharmaceutical composition, comprising nanoparticles and/or nanoparticles' aggregates such as defined hereinabove, preferably together with a pharmaceutically acceptable carrier or vehicle.

In particular, herein described is a composition for use for preventing or treating/for use in prevention or treatment of a neurological disease as herein described or at least one symptom thereof in a subject without exposure of the nanoparticles or nanoparticles' aggregates to an electric field, and preferably without exposure thereof to any other external activation source such as a light source, a magnetic field, or an ultrasound source, wherein the composition comprises, or consists of, nanoparticles and/or nanoparticles' aggregates and a pharmaceutically acceptable support, and wherein the nanoparticle's or nanoparticles' aggregate's material is typically selected from a conductor material, a semiconductor material, an insulator material with a dielectric constant $\varepsilon_{ijk}$ equal to or above 200, and an insulator material with a dielectric constant $\varepsilon_{ijk}$ equal to or below 100 as herein above described and explained. In a preferred aspect, the composition comprises, or consists of, at least two distinct nanoparticles and/or nanoparticles' aggregates, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100.

In a typical aspect of the invention, the herein described nanoparticle(s) or aggregate(s) of nanoparticles are not used as carrier(s) of (active) therapeutic compound(s) or drug(s).

In a particular aspect, the composition can comprise the nanoparticles or nanoparticles' aggregates of the invention together with a therapeutic agent. In the context of the present invention, such a therapeutic agent is typically not a nanoparticle nor a nanoparticles' aggregate. The therapeutic agent can be selected from any drug used in a neurological disorder treatment. The therapeutic agent is typically selected from antipsychotics, anti-dopaminergics, dopaminergics, anti-cholinergics, cholinergics, anti-glutamatergics, glutamatergics, acetylcholinesterase inhibitors, N-methyl D-aspartate (NMDA) receptor antagonists, gamma-amino butyric acid (GABA) agonists, botulinum toxin, anti-dystonic drugs, anti-epileptic drugs, anticonvulsants, mood stabilizers, antidepressants and sedatives.

The composition can be in the form of a solid, liquid (particles in suspension), aerosol, gel, paste, and the like. Preferred compositions are in a liquid or a gel form. Particularly preferred compositions are in liquid form.

The pharmaceutically acceptable support or carrier which is employed can be any classical support for the skilled person, such as for example a saline, isotonic, sterile, buffered solution, a non-aqueous vehicle solution and the like.

The composition can also comprise stabilizers, sweeteners, surfactants, polymers and the like. It can be formulated for example as ampoule, aerosol, bottle, tablet, capsule, by using techniques of pharmaceutical formulation known by the skilled person.

The nanoparticles or nanoparticles' aggregates of the invention can be administered to the subject using different possible routes such as intra-cranial, intra venous (IV), airways (inhalation), intra-thecal, intra-ocular or oral route (per os), intra-cerebroventricular (ICV), preferably using intra-cranial or intra-thecal. Repeated injections or administrations of nanoparticles can be performed, when appropriate. Preferably, the nanoparticles or nanoparticles' aggregates are to be administered once.

The nanoparticles and/or nanoparticles' aggregates once administered typically interact with the neurons' subject. In a preferred aspect, this interaction is a prolonged interaction, i.e. an interaction of several hours, days, weeks or months. In a particular aspect, the nanoparticles or nanoparticles' aggregates remain in the subject.

The herein described nanoparticles or nanoparticles' aggregates and compositions comprising such nanoparticles or nanoparticles' aggregates are for use in a subject, typically for use in an animal, preferably in a mammal, even more preferably in a human being, typically a human patient, whatever its age or sex.

Typical quantity(ies) of nanoparticles or aggregates of nanoparticles to be administered in the cerebral cortex, hippocampus and/or amygdala of the subject is(are) between $10^5$ and $10^{17}$, between $10^5$ and $10^{16}$ or between $10^5$ and $10^{15}$, preferably between $10^7$ and $10^{14}$, more preferably between $10^9$ and $10^{12}$. Also, typical quantity(ies) of nanoparticles or aggregates of nanoparticles to be administered in the cerebral cortex, hippocampus and/or amygdala of the subject is(are) between $10^2$ and $10^{12}$ nanoparticles or aggregates of nanoparticles per $cm^3$.

Typical quantity(ies) of nanoparticles or aggregate of nanoparticles to be administered in the deep brain of the subject is(are) between $10^4$ and $10^{17}$, between $10^4$ and $10^{16}$, between $10^4$ and $10^{15}$ or between $10^4$ and $10^{14}$, preferably between $10^6$ and $10^{12}$, more preferably between $10^8$ and $10^{11}$. Also, typical quantity(ies) of nanoparticles or aggregates of nanoparticles to be administered in the deep brain of the subject is(are) between $10^1$ and $10^{11}$ nanoparticles or aggregates of nanoparticles per $cm^3$.

Also, herein described is a method for preventing or treating a neurological disease or at least one symptom thereof in a subject, wherein the method comprises a step of administering anyone of the herein described nanoparticles or nanoparticles' aggregates to the subject. This method typically does not include any step of exposing the subject, and more precisely the nanoparticles or nanoparticles' aggregates which have been administered to said subject, to an electric field, and preferably also does not include any step of exposing the subject, and more precisely the nanoparticles or nanoparticles' aggregates which have been administered to said subject, to any other external activation source such as a light source, a magnetic field, or an ultrasound source.

A further object herein described relates to a kit comprising, or consisting of, at least two distinct nanoparticles and/or at least two distinct nanoparticles' aggregates as herein described, each nanoparticle or nanoparticles' aggregate consisting of a distinct material typically selected from a conductor material, a semiconductor material, an insulator material with a dielectric constant $\varepsilon_{ijk}$ equal to or above 200 and an insulator material with a dielectric constant $\varepsilon_{ijk}$ equal to or below 100 as herein described.

In a particular embodiment, the kit comprises, in distinct containers, distinct nanoparticles and/or nanoparticles aggregates as herein described (which are intended to be contacted, typically mixed, either in situ, i.e. on the target site, or in vitro or ex vivo before deposition of the mixture on the target site). A further object relates to a kit further comprising at least one additional therapeutic agent, distinct from the nanoparticles or nanoparticles aggregates as herein described, such as an antipsychotic, anti-dopaminergic, dopaminergic, anti-cholinergic, cholinergic, anti-glutamatergic, glutamatergic, acetylcholinesterase inhibitor, N-methyl D-aspartate (NMDA) receptor antagonist, gamma-amino butyric acid (GABA) agonist, botulinum toxin, anti-dystonic drug, anti-epileptic drug, anticonvulsants, mood stabilizer, antidepressant and sedative, that the skilled person of the art will be able to select depending on the nature of the targeted disease. As explained herein above, such an additional therapeutic agent is typically not a nanoparticle nor a nanoparticles' aggregate.

Also herein described is the use, in vivo, in vitro or ex vivo, of such a kit in a method for preventing or treating a neurological disease as herein described or at least one symptom thereof in a subject, without exposure of the nanoparticles or nanoparticles' aggregates administered to the subject to an electric field, and preferably without exposure thereof to any other external activation source such as a light source, a magnetic field, or an ultrasound source. Also, herein disclosed is a kit as herein described for use in prevention or treatment of a neurological disease or of at least one symptom thereof in a subject, without exposure of the nanoparticles or nanoparticles' aggregates administered to the subject to an electric field, and preferably without exposure thereof to any other external activation source such as a light source, a magnetic field, or an ultrasound source.

At the neuron level, nanoparticles have been described to enhance or inhibit electrical excitability of neurons. For instance, zinc oxide, carbon nanotubes and gold nanoparticles were found to enhance electrical excitability of neurons whereas, copper oxide, silver, carbon black, iron oxide and titanium oxide were found to inhibit electrical excitability of neurons (Polak P & Shefi O. *Nanomedicine: Nanotechnology, Biology and Medicine* 11 (2015) 1467-1479, *Nanometric agents in the service of neuroscience: Manipulation of neuronal growth and activity using nanoparticles*).

Systemic influence studies on neuronal systems of coated silver nanoparticles (cAgNP)—using amphiphilic polymer polyethylene glycol—[cAgNP with hydrodynamic diameter of 13 nm±2 nm (dynamic light scattering technique) and zeta potential of −69 mV (Zetasizer Nano) in pure water]) showed that the nanoparticles induced changes in mechanism affecting excitability. Besides, neuron network simulation showed that locally cAgNP-induced changes result in changes in network activity in the entire network, indicating that local application of cAgNP may influence the activity throughout the network (Busse M. et al. *International Journal of Nanomedicine* 2013:8 3559-3572, *Estimating the modulatory effects of nanoparticles on neuronal circuits using computational upscaling*).

Also, increased excitability of neurons associated with intracellular gold nanoparticles has been described to potentially have deleterious effects on neurons under pathological conditions such as seizure (Jung S, et al. *PLOS ONE* 2014, 9(3) e91360, *Intracellular gold nanoparticles increase neuronal excitability and aggravate seizure activity in the mouse brain*).

The nanoparticles or nanoparticles' aggregates of the present invention are for use for preventing or treating/for use in prevention or treatment of a neurological disease or at least one symptom thereof, by normalizing synchronization of oscillations within and/or between neuronal networks within and/or between distinct regions of the brain, without exposure of said nanoparticles or nanoparticles' aggregates to an electric field, and preferably without exposure thereof to any other external activation source such as a light source, a magnetic field, or an ultrasound source.

Figure 2:
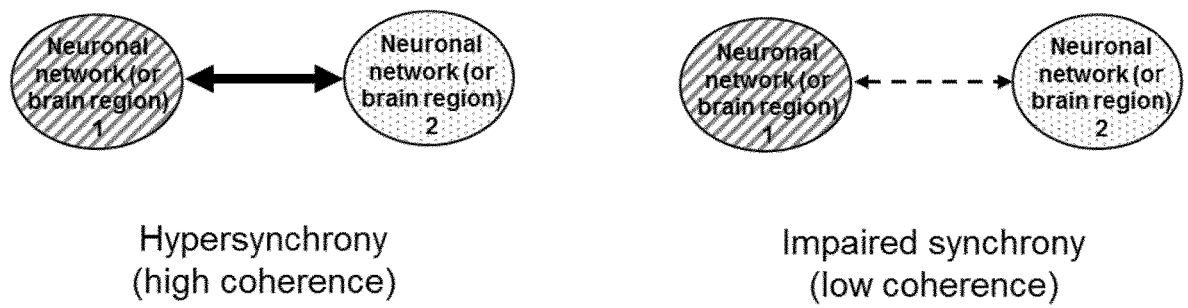
Figure 3:
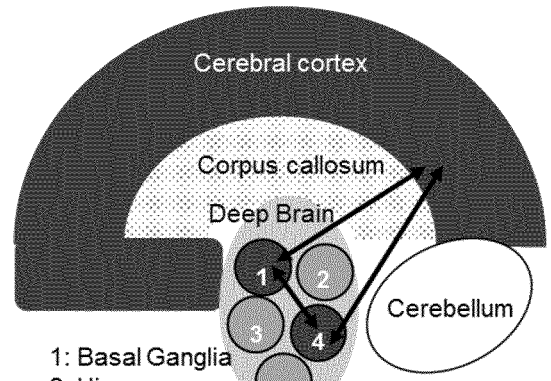
Figure 3:
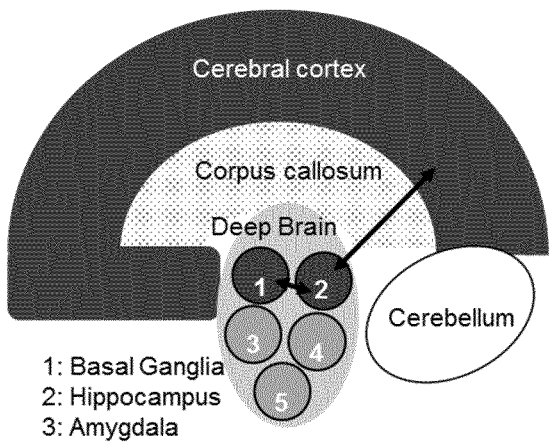
Figure 3:
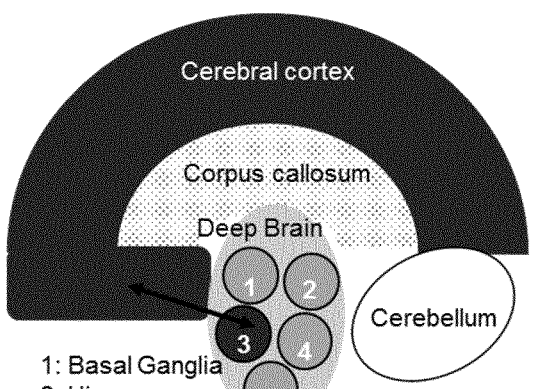
Figure 3:
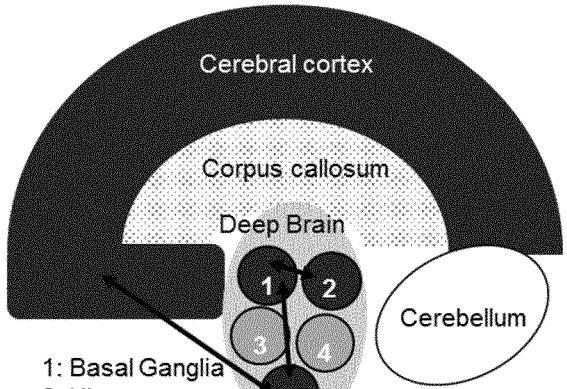
Figure 4:
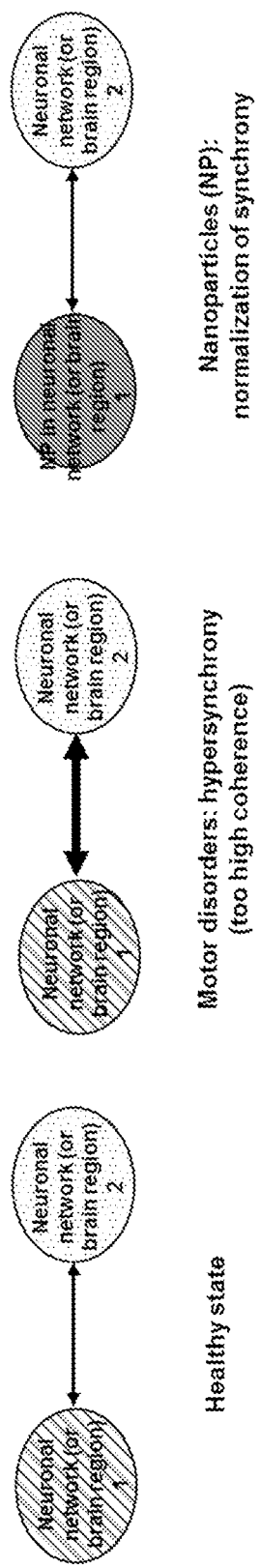
Figure 5:
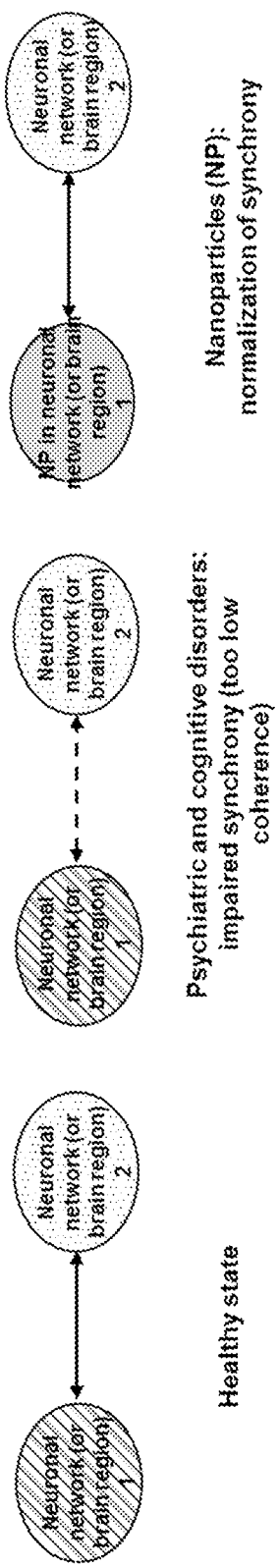

As illustrated in FIGS. 2 and 3, communication within and/or between distinct regions of the brain is affected in neurological disease. According to the neurological disorder and associated symptoms, exposition of specific area of the brain to nanoparticles of the present invention, will improve communication via normalization of the synchronization of oscillations within and/or between neuronal networks within and/or between distinct regions of the brain (i.e. normalization of the coherence) (FIGS. 4 and 5).

The examples which follow and their corresponding figures illustrate the invention without limiting the scope thereof.

FIGURES

FIG. 1. Schematic representation of the brain (sagittal plane).

FIG. 2. Hypersynchrony and impaired synchrony between two neuronal networks.

FIG. 3. Brain areas involved in various neurological diseases.

FIG. 4. Effect of nanoparticles (NP) on normalization of hypersynchrony (motor disorders).

FIG. 5. Effect of nanoparticles (NP) on normalization of impaired synchrony (psychiatric and cognitive disorders).

Figure 6:
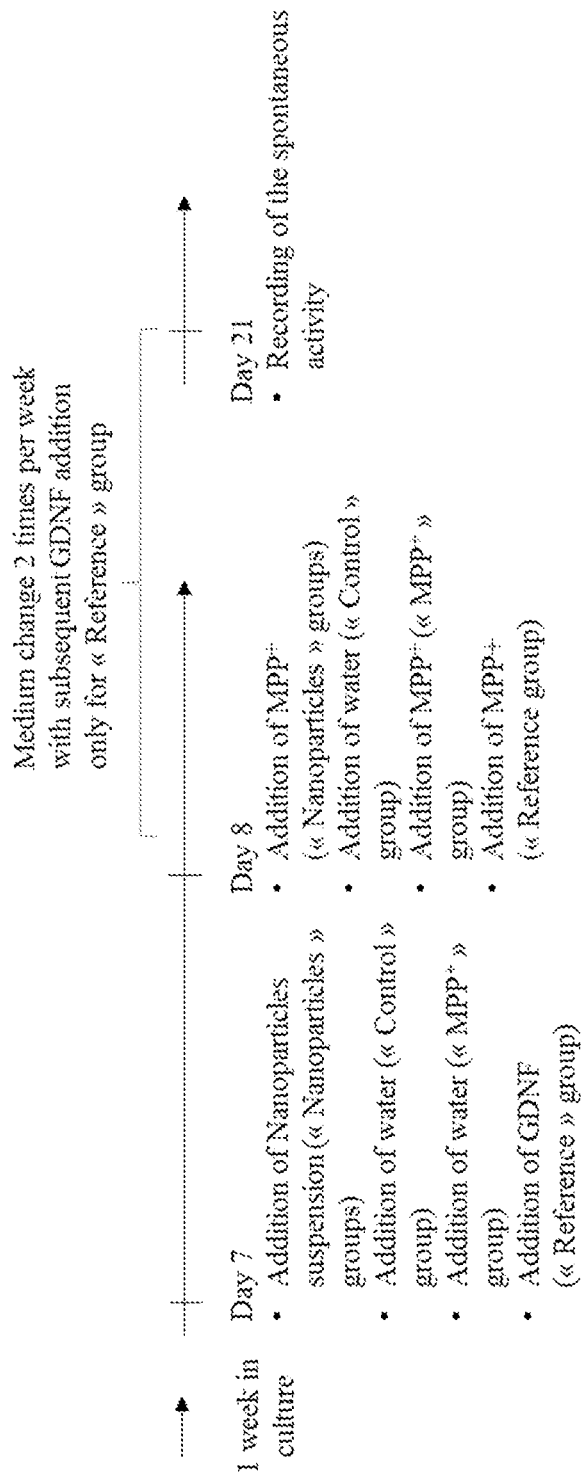

FIG. 6. Experimental scheme of induction of Parkinson's disease with MPP$^+$ treatment and electrical activity recording.

The mouse ventral midbrain/cortex co-cultures were prepared from E14.5 NMRI mice and cultured on 48 well MEAs for 3 weeks (total culture period). The cultures were treated after 7 days in culture (day 7) with the nanoparticles' suspensions ("Nanoparticles" groups), GDNF (20 ng/ml) ("Reference" group) or water ("Control" group and "MPP$^+$" group) and at day 8 with MPP (20 µM) ("Nanoparticles" groups, "Reference" group and "MPP$^+$" group) or water ("Control" group). The spontaneous activity was recorded at day 21.

Figure 7:
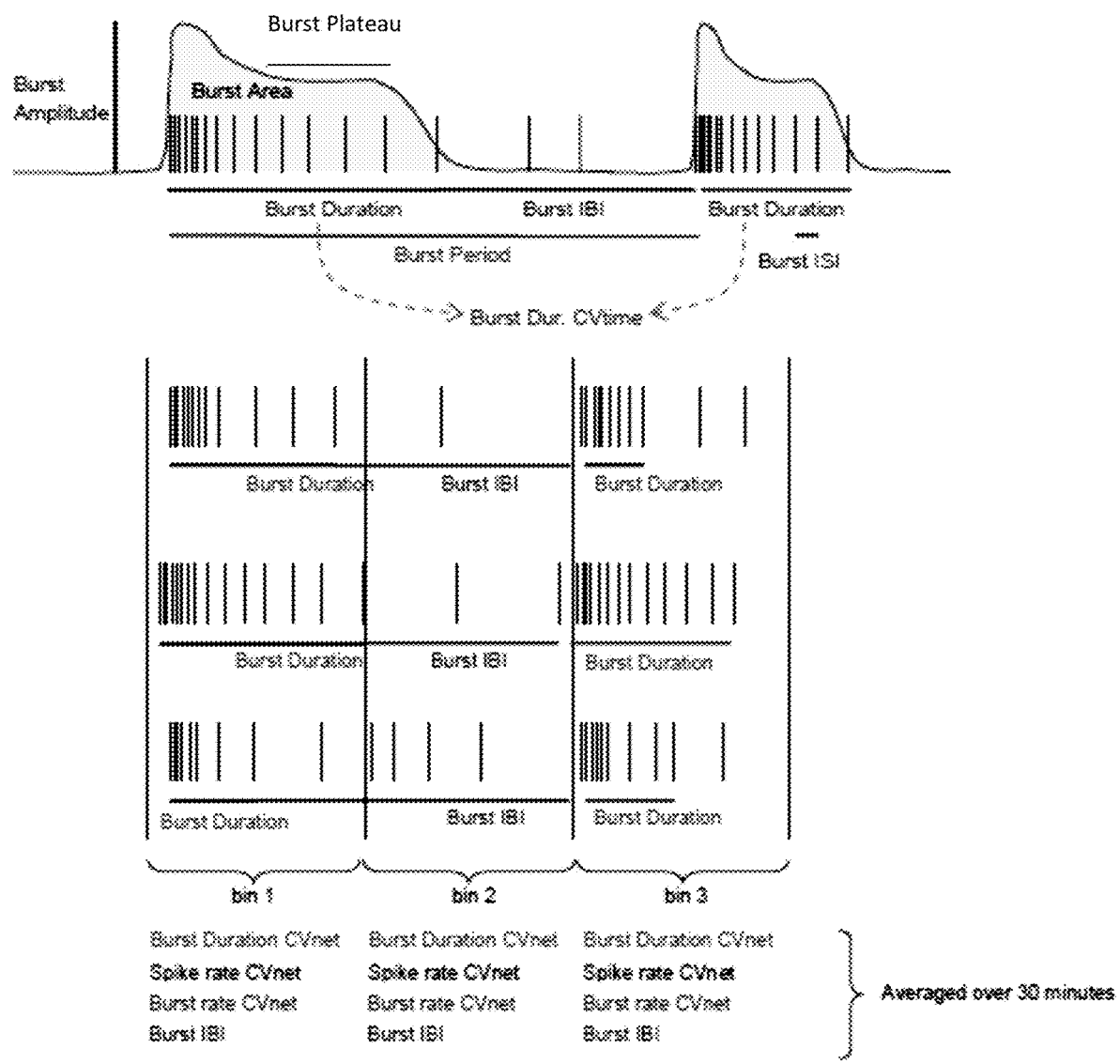

FIG. 7. Scheme of two simplified bursts outlining some of the parameters that can be extracted from the electrical activity recording. Parameters describing general activity (spike, burst, inter burst interval (IBI) and burst period) and burst structure (burst duration, burst plateau, burst amplitude, burst inter spike interval (ISI) and burst area) are indicated. Standard deviations (SD) of these parameters are measures for regularity of general activity and burst structure respectively. Coefficient of variation in time (CVtime) reflects the temporal regularity of the activity pattern of each unit. CVtime is calculated by the ratio of parameter's standard deviation and mean. Coefficient of variation among the network (CVnet) reflects synchronization among neurons within the network. CVnet is calculated by the ratio of parameter's standard deviation by mean over the network. Large CVnet values imply a wide range of variation in the activity across the network, meaning less synchronization.

Figure 8:
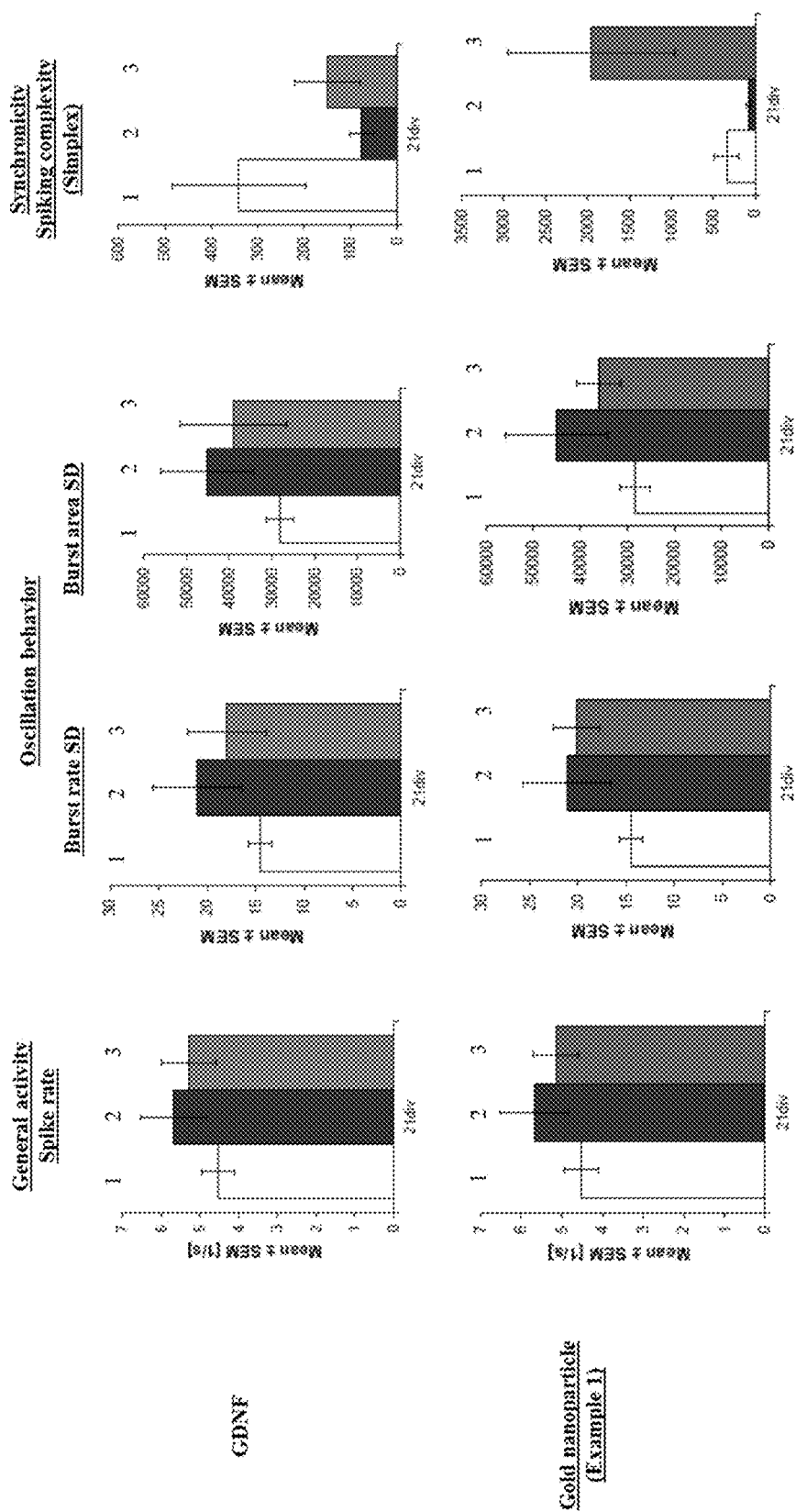
Figure 8:
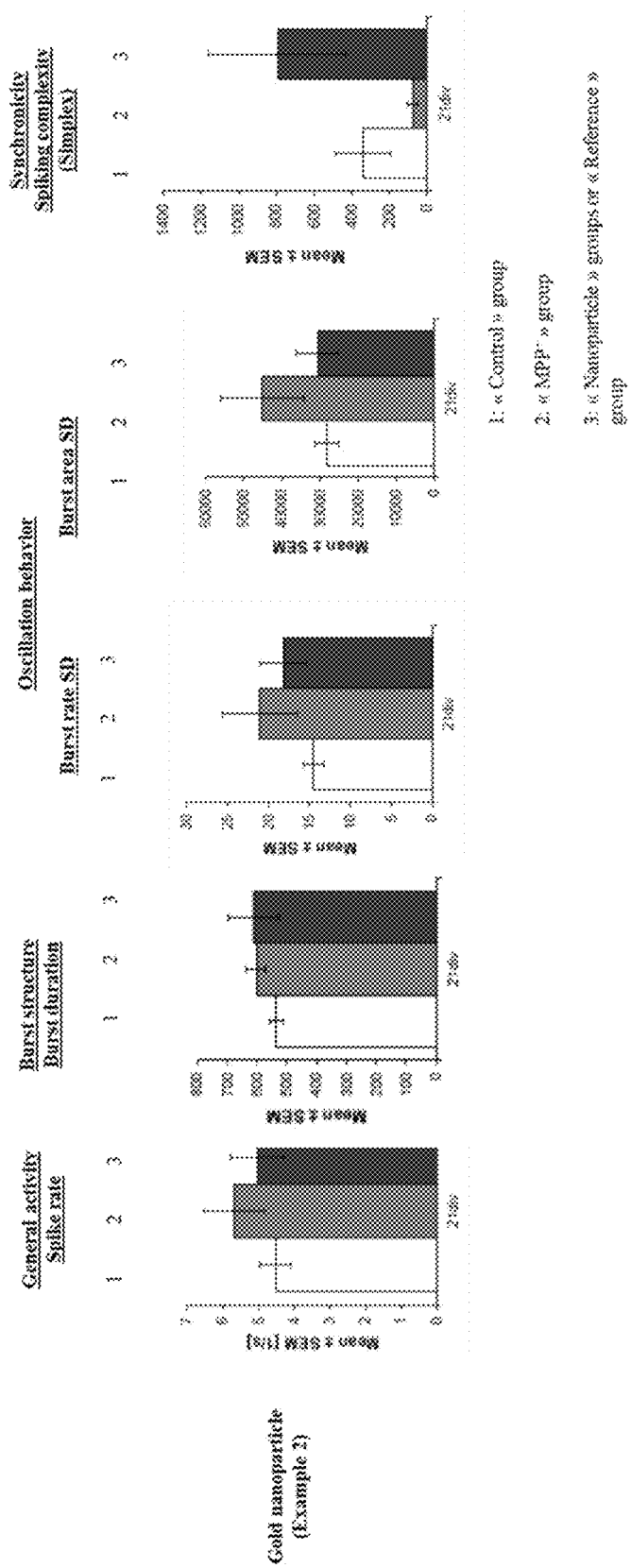

FIG. 8. Functional effects observed in "Nanoparticles" groups (nanoparticles from examples 1 and 2) and "Reference" group compared to "Control" group and "MPP$^+$" group on midbrain/cortex network activity. The data show MPP$^+$-induced functional effects and demonstrate the prevention/rescue efficacy allowed by the nanoparticles of the invention or by GDNF (i.e. ability to prevent/rescue functional effects to a level similar to that of "Control" group).

Figure 9:
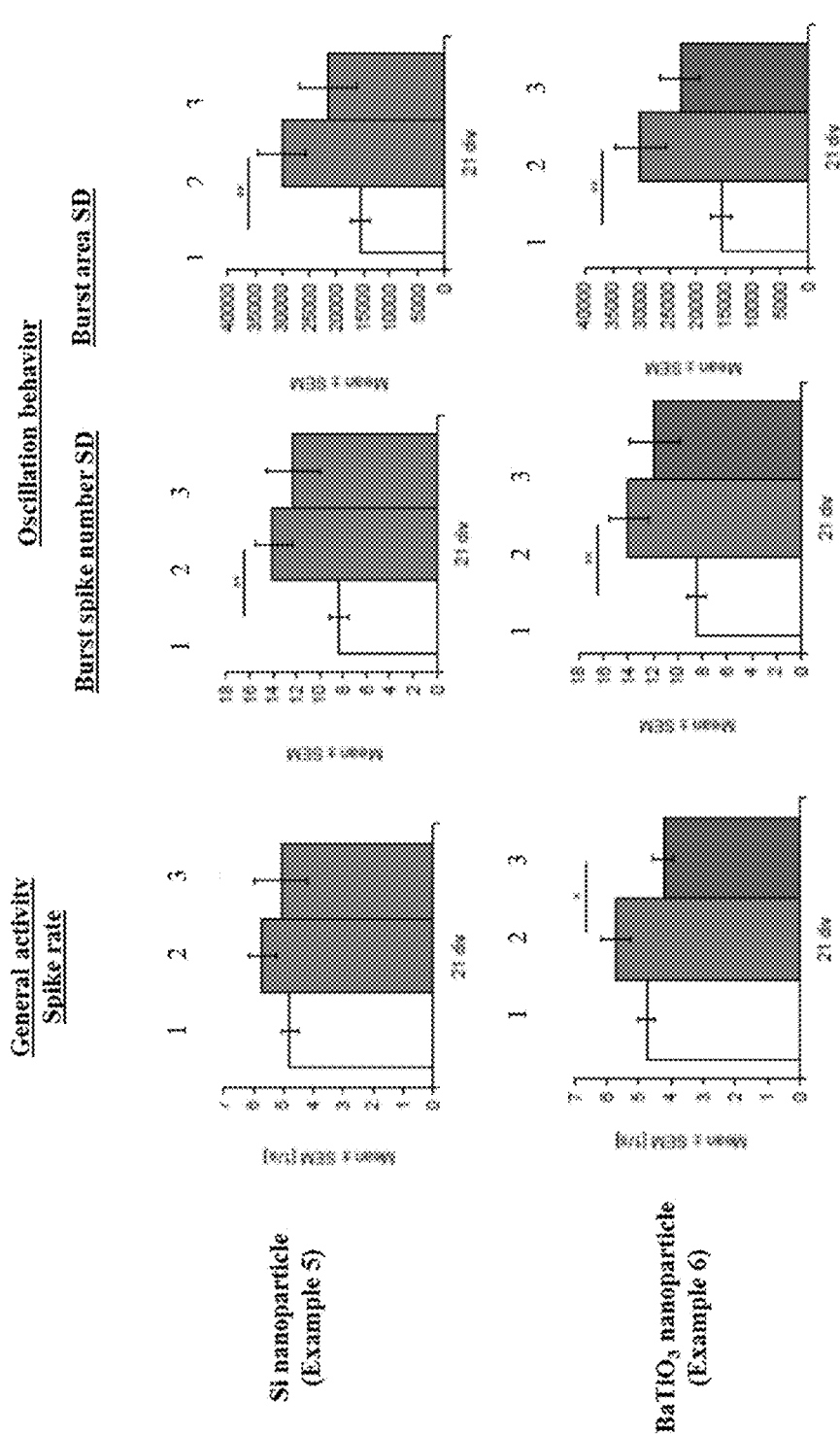

FIG. 9. Functional effects observed in "Nanoparticles" groups (nanoparticles from examples 5 and 6) compared to "Control" group and "MPP$^+$" group on midbrain/cortex network activity. The data show MPP$^+$-induced functional effects and demonstrate the prevention/rescue efficacy allowed by the nanoparticles of the invention (i.e. ability to prevent/rescue functional effects to a level similar to that of "Control" group).

Figure 10:
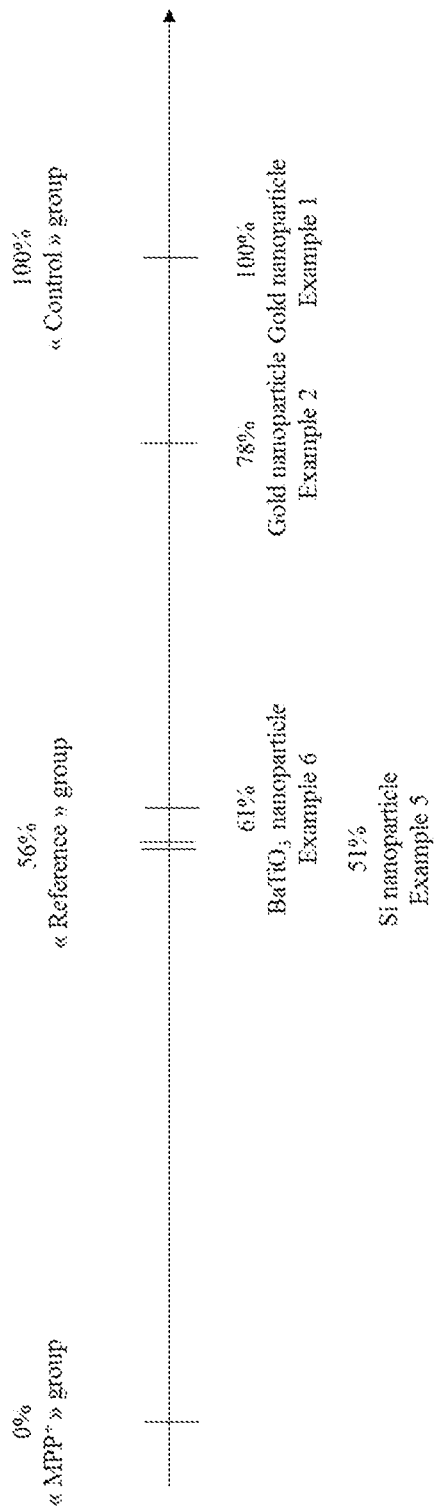

FIG. 10. Effect Score analysis for the "Nanoparticles" groups, "Reference" group, "Control" group and "MPP$^+$" group.

Figure 11:
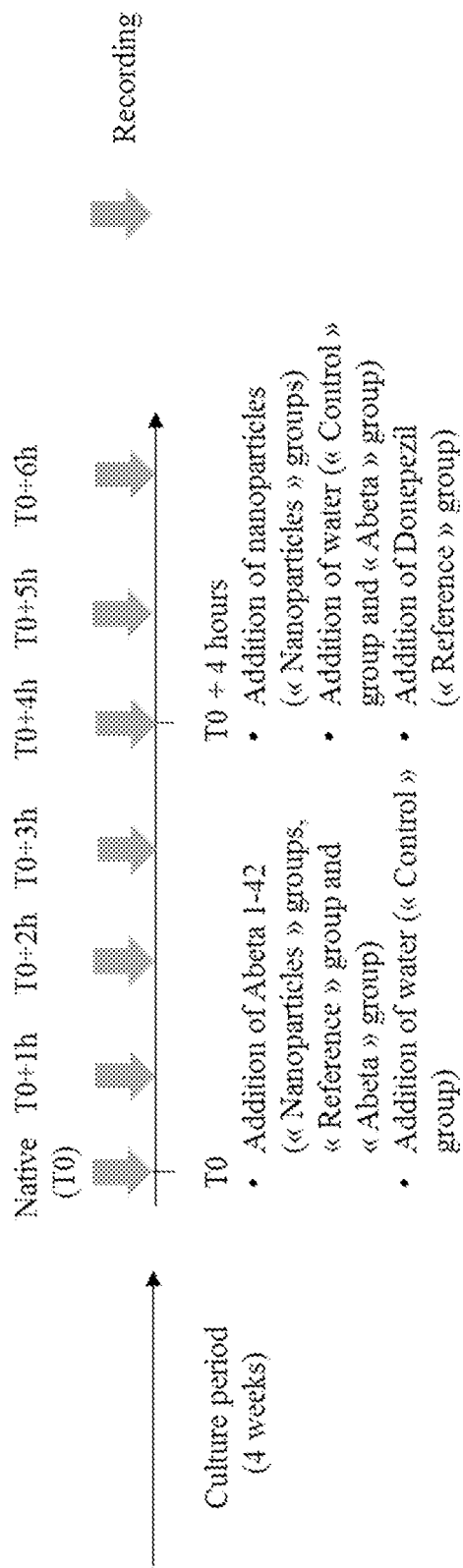

FIG. 11. Experimental scheme of induction of Alzheimer's disease with amyloid beta 1-42 (Abeta 1-42), treatment and electrical activity recordings. After 4 weeks in cultures (culture period), Abeta 1-42 (100 nM) ("Nanoparticle" group, "Reference" group and "Abeta" group) or water ("Control" group) (T0) were added to the neuronal network. Four (4) hours later, the nanoparticles' suspensions ("Nanoparticle" groups), Donepezil (300 nM) ("Reference" group) or water ("Control" group and "Abeta" group) were added. The spontaneous activity was recorded as follow:
at T0 (prior addition of Abeta 1-42)
at T0+1 h, +2 h, +3 h, +4 h (prior to nanoparticles, donepezil or water addition), +5 h, and +6 h.

Figure 12:
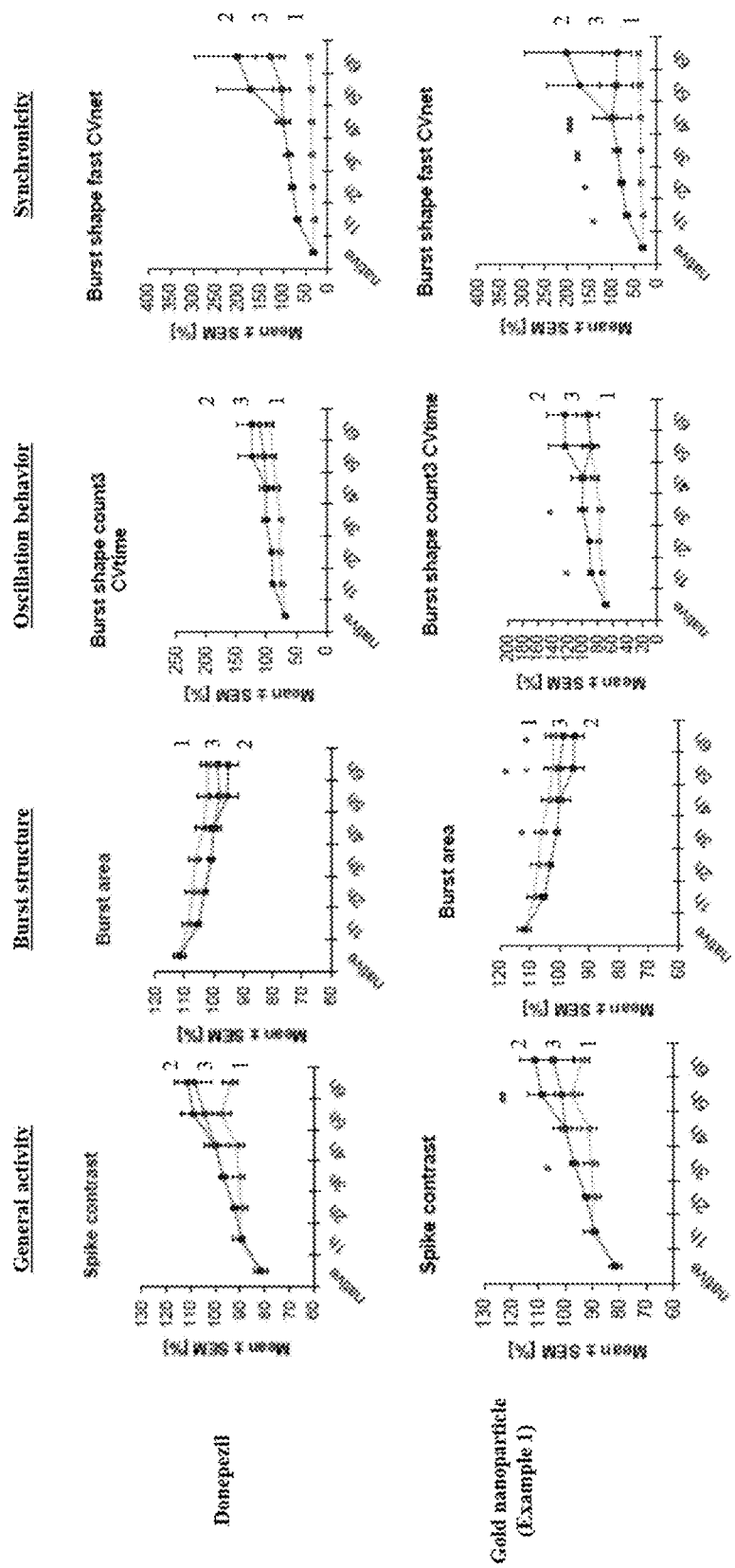
Figure 12:
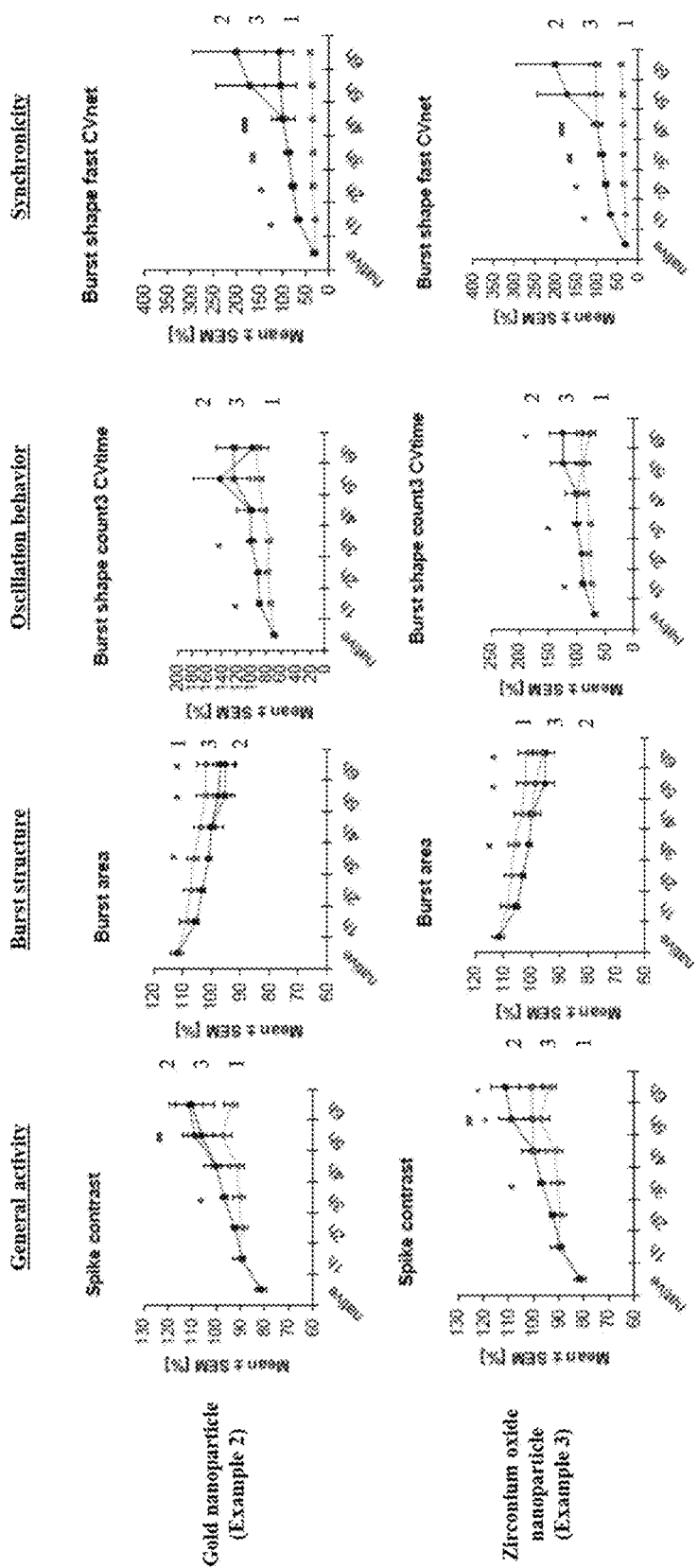
Figure 12:
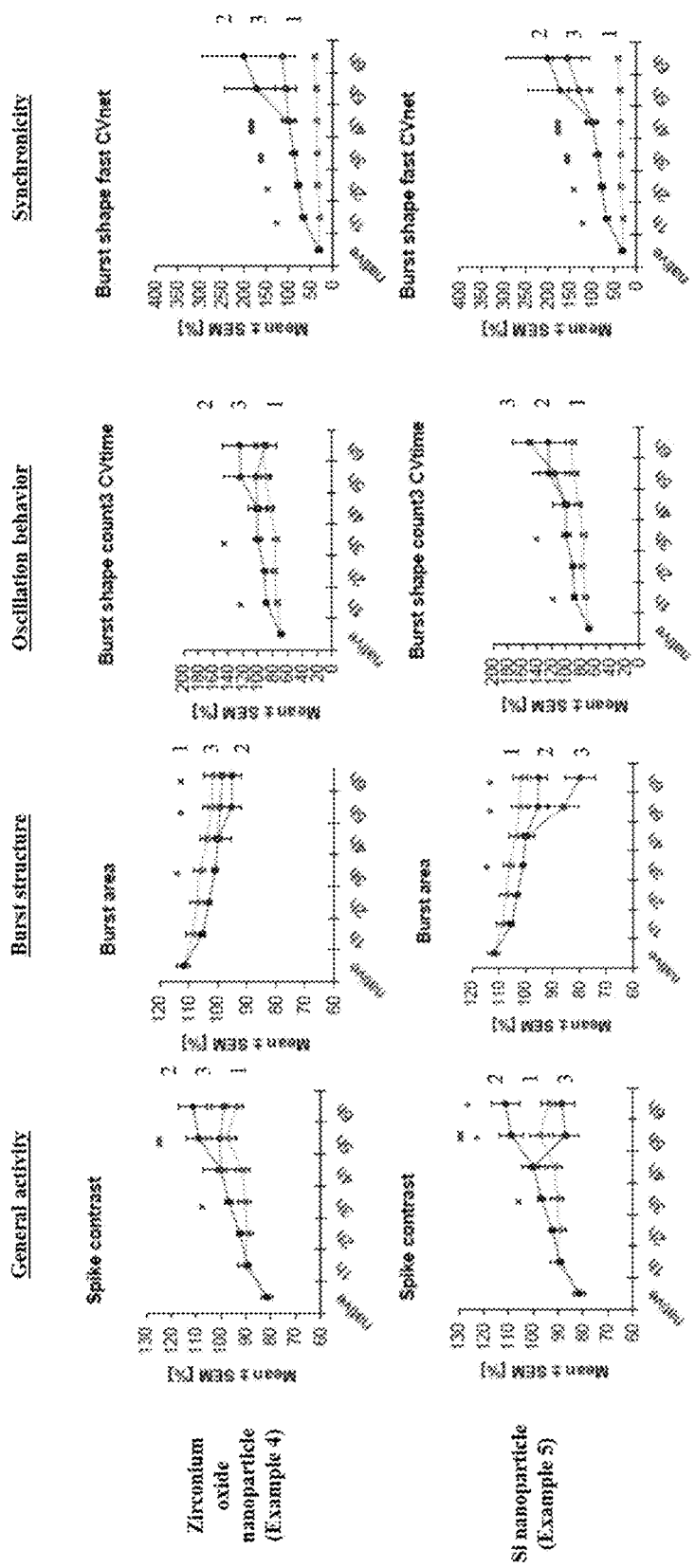
Figure 12:
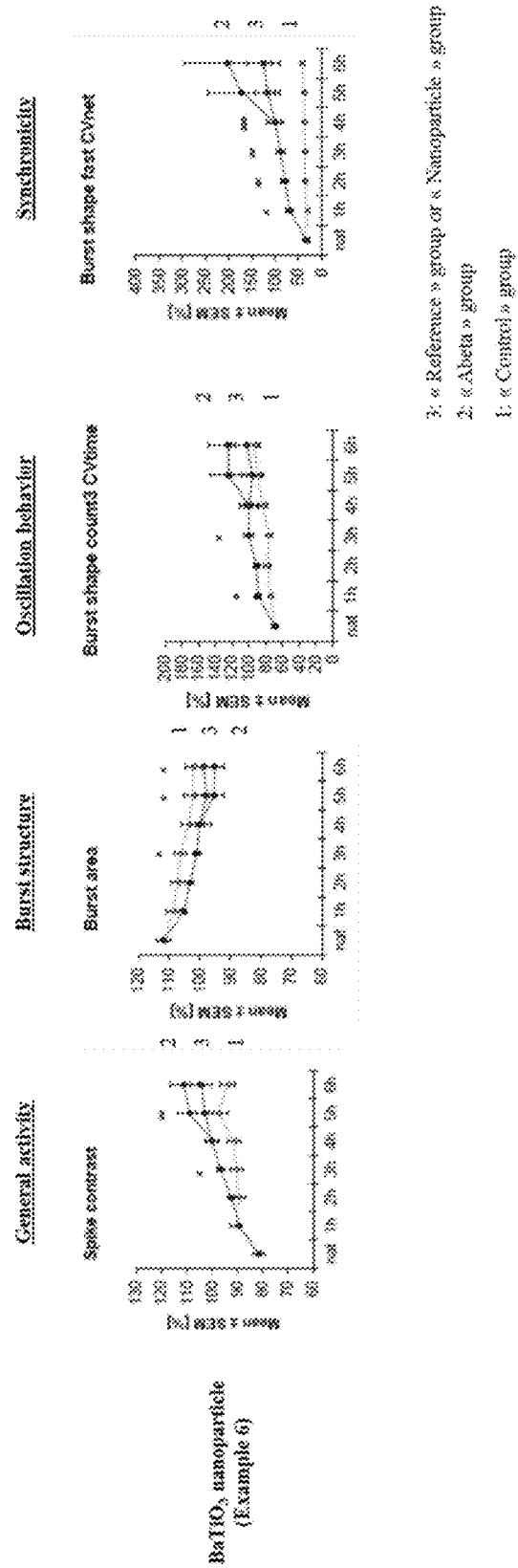

FIG. 12. Functional effects observed in "Nanoparticles" groups and "Reference" group compared to "Control" group and "Abeta 1-42" group on cortex network activity. The data show Abeta 1-42 functional effects and demonstrate the rescue efficacy allowed by the nanoparticles of the invention or by donepezil (i.e. ability to rescue functional effects to a level similar to that of the "Control" group).

Figure 13:
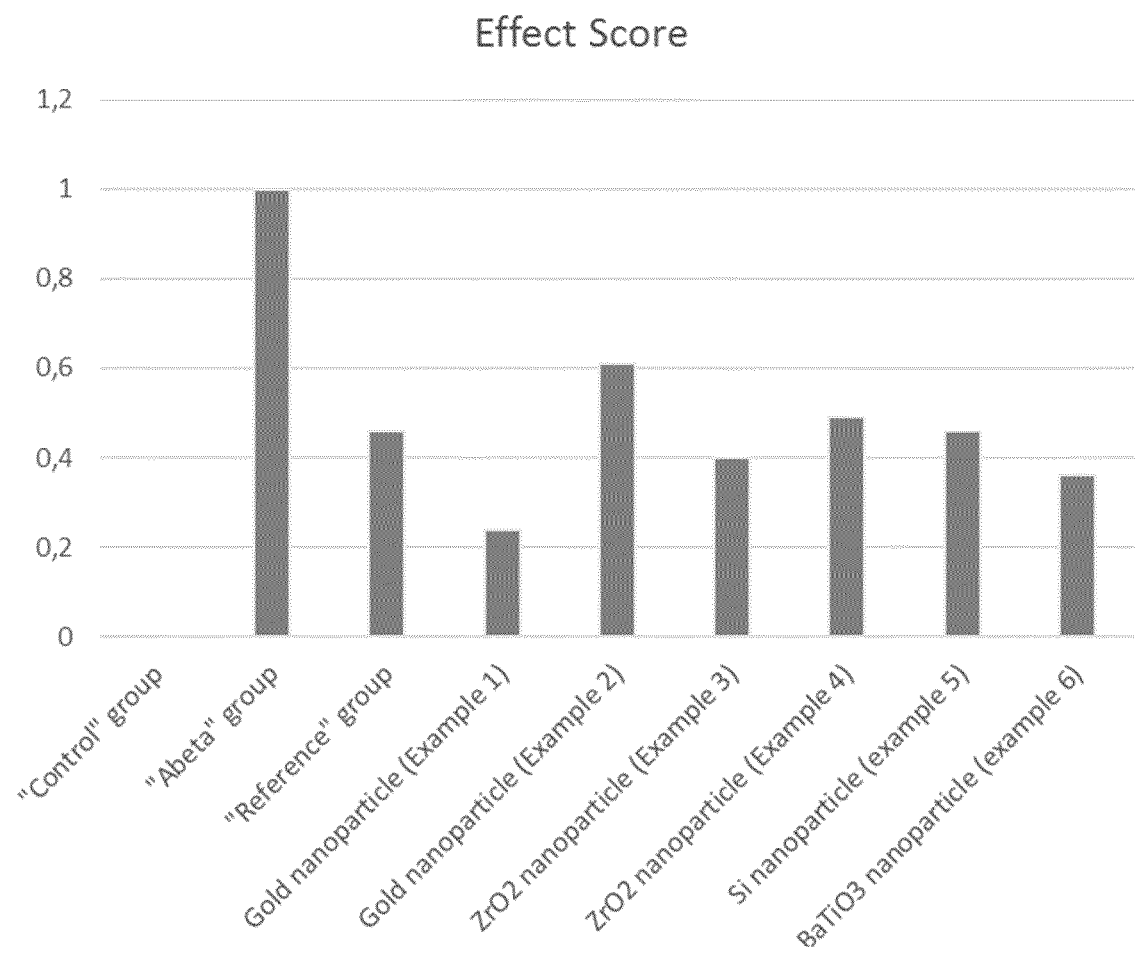

FIG. 13. Effect Score analysis for the "Nanoparticles" groups, "Reference" group, "Control" group (Effect Score=0) and "Abeta" group (Effect Score=1).

Figure 14:
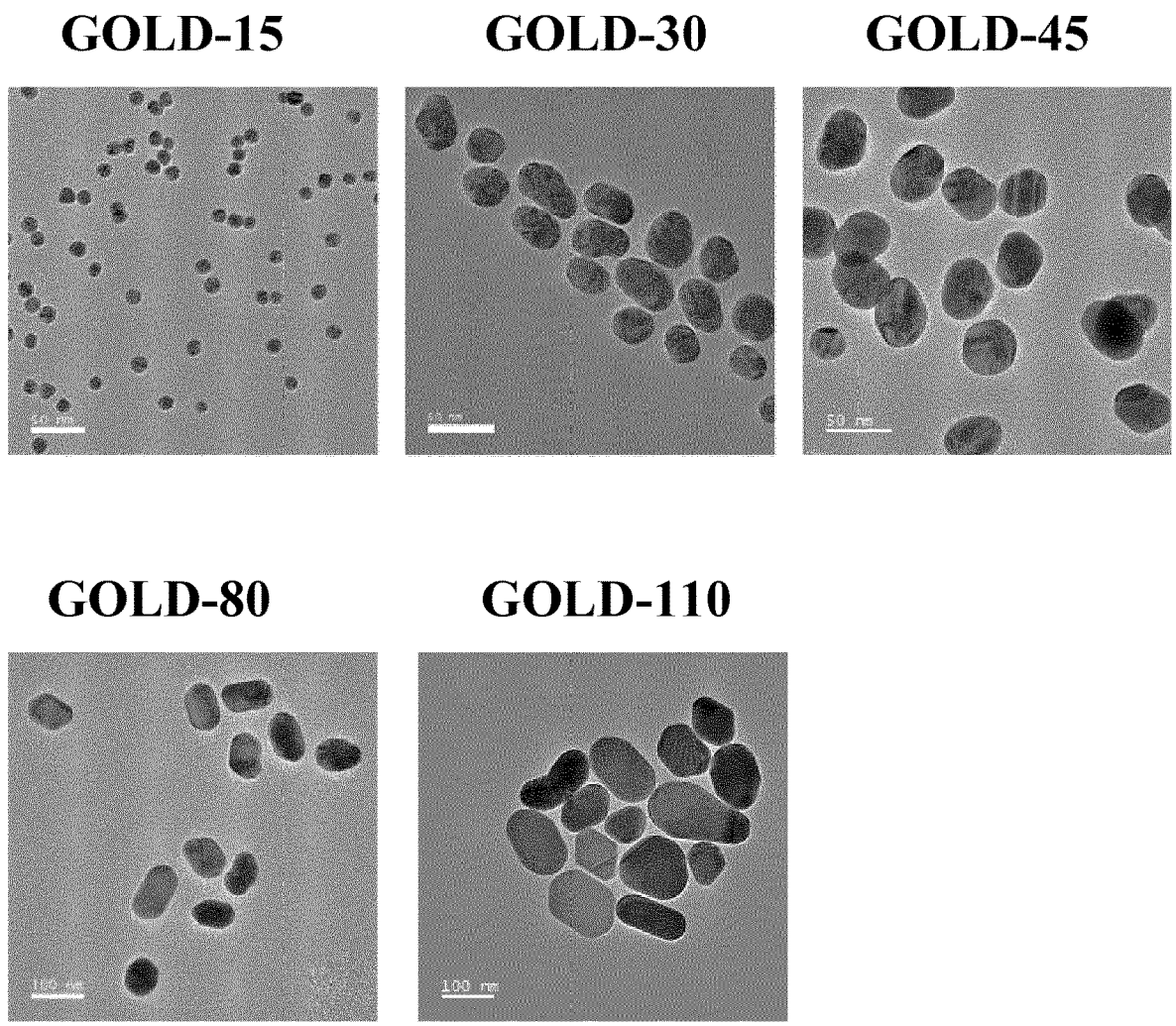

FIG. 14. Representative TEM images of gold nanoparticles from examples 9, the median largest size of the core of the nanoparticles of the population being equal to 108 nm (GOLD-110), 83 nm (GOLD-80), 45 nm (GOLD-45), 34 nm (GOLD-30) and 15 nm (GOLD-15) respectively.

Figure 15:
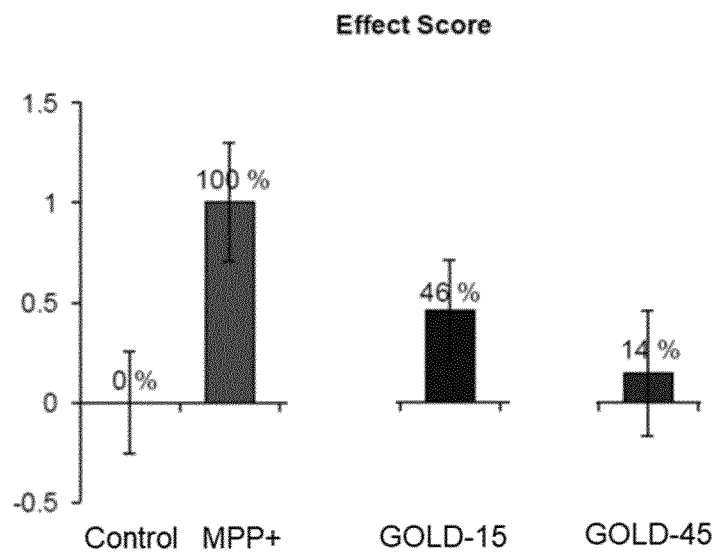

FIG. 15. Effect Score analysis for the "Nanoparticles" groups (GOLD-45 and GOLD-15 nanoparticles from example 9), "Control" group (Effect Score=0) and "MPP+" group (Effect Score=1).

Figure 16:
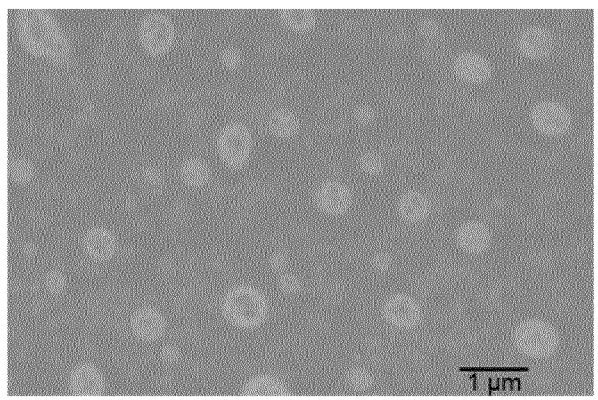

FIG. 16. Representative scanning electron microscopy (SEM) image of PEDOT nanoparticles from example 11.

Figure 17:
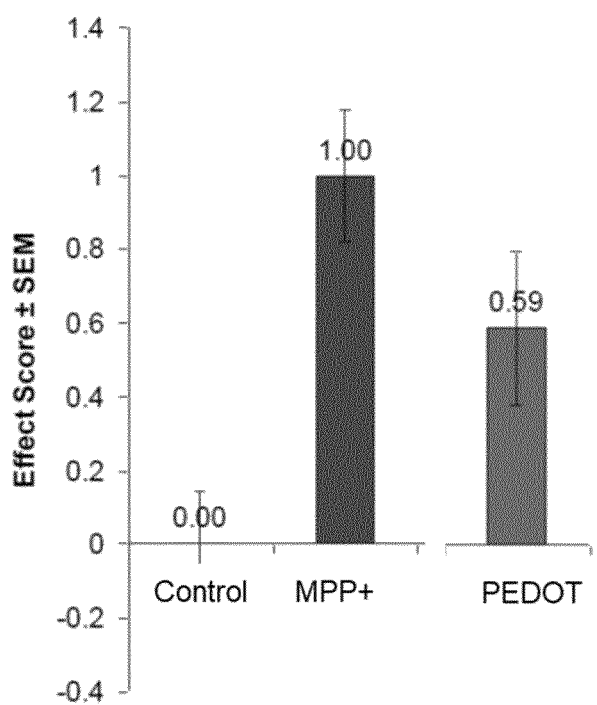

FIG. 17. Effect Score analysis for the "Nanoparticles" groups (PEDOT nanoparticles from example 11), "Control" group (Effect Score=0) and "MPP+" group (Effect Score=1).

EXAMPLES

In Vitro Studies of Neurons

At the neuron level, Patch clamp technique is very useful for detecting action potentials, as it allows simultaneous direct measurement and control of membrane potential of a neuron. This technique is used to assess the effects of nanoparticles on a single neuron.

In Vitro Studies of a Network of Neurons

Dissociated neuronal cultures coupled to multi electrode arrays (MEAs) are widely used to better understand the complexity of brain networks. In addition, the use of dissociated neuronal assemblies allows the manipulation and control of the network's connectivity. The MEA system enables non-invasive, long-lasting, simultaneous extracellular recordings from multiple sites in the neuronal network in real time, increasing spatial resolution and thereby providing a robust measure of network activity. The simultaneous gathering of action potential and field potential data over long periods of time allows the monitoring of network functions that arise from the interaction of all cellular mechanisms responsible for spatio-temporal pattern generation (Johnstone A. F. M et al., *Neurotoxicology*, 2010, 31, 331-350: *Microelectrode arrays: a physiologically based neurotoxicity testing platform for the 21st century*). Compared to patch-clamp and other single electrode recording techniques, MEA measures responses of a whole network, integrating global information on the interaction of all receptors, synapses and neuronal types which are present in the network (Novellino A. et al., *Frontiers in Neuroengineering*, 2011, 4(4), 1-14: *Development of micro-electrode array based tests for neurotoxicity: assessment of interlaboratory reproducibility with neuroactive chemicals*). As such, MEA recordings have been employed to understand neuronal communication, information encoding, propagation, and processing in neuronal cultures (Taketani, M., and Baudry, M. (2006). *Advances in Network Electrophysiology*. New York, N.Y.: Springer; Obien et al., *Frontiers in Neurosciences*, 2015, 8(423): *Revealing neuronal functions through microelectrode array recordings*). The MEA technology is a sophisticated phenotypic high-content screening method to characterize functional changes in network activity in electrically active cell cultures and it is very sensitive to neurogenesis, as well as neuroregenerative and neurodegenerative aspects. Moreover, neuronal networks grown on MEAs are known as being capable of responding to neuroactive or neurotoxic compounds in approximately the same concentration ranges that alter functions of an intact mammalian nervous system (Xia et al., *Alcohol*, 2003, 30, 167-174: *Histiotypic electrophysiological responses of cultured neuronal networks to ethanol*; Gramowski et al., *European Journal of Neuroscience*, 2006, 24, 455-465: *Functional screening of traditional antidepressants with primary cortical neuronal networks grown on multielectrode neurochips*; Gramowski et al., *Frontiers in Neurology*, 2015, 6(158): *Enhancement of cortical network activity in vitro and promotion of GABAergic neurogenesis by stimulation with an electromagnetic field with 150 MHz carrier wave pulsed with an alternating 10 and 16 Hz modulation*).

This technique is used to assess the effect of nanoparticles on neuronal network(s).

In Vivo Studies of a Network of Neurons

An appropriate animal model is considered to assess the effect on neuronal networks of animals of nanoparticles of the invention.

For instance, mouse models of Parkinson's disease are used to assess the effects of nanoparticles on the relief of behavior impairment (motor disorders). Also, rat or mouse models of Alzheimer's disease are used to assess the effects of nanoparticles on the spatial learning and memory dysfunction (cognitive disorders) of animals.

Example 1. Nanoparticles Prepared with a Conductor Material: Synthesis of Gold Nanoparticles Coated with a Biocompatible Coating Having a Neutral Surface Charge Gold nanoparticles were synthesized by reducing a gold chloride salt ($HAuCl_4$) with a capping agent (sodium citrate) (protocol was adapted from G. Frens *Nature Physical Science* 241 (1973) 21). In a typical experiment, $HAuCl_4$ solution was heated to boiling. Subsequently, sodium citrate solution was added. The resulting solution was maintained under boiling for an additional period of 5 minutes.

A 0.22 μm filtration (filter membrane: poly(ether sulfone) (PES)) of the nanoparticles' suspension was performed and gold concentration in suspension was determined by a UV-visible spectroscopy assay at 530 nm.

A surface coating was performed using α-methoxy-ω-mercaptopoly(ethylene glycol) 20 kDa ("thiol-PEG20 kDa"). A sufficient amount of "thiol-PEG 20 kDa" was added to the nanoparticles' suspension to reach at least half a monolayer coverage (2.5 molecules/$nm^2$) on the gold nanoparticle surface. pH was adjusted between 7 and 7.2, and the nanoparticles' suspension was stirred overnight.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration: [Au]=0.1 g/L). The hydrodynamic diameter of the so obtained biocompatible gold nanoparticles in suspension was found equal to 118 nm, with a polydispersity index (dispersion of the nanoparticles' population in size) of 0.13.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [Au]=0.1 g/L). The zeta potential at pH 7 was found equal to −1 mV.

Example 2. Nanoparticles Prepared with a Conductor Material: Synthesis of Gold Nanoparticles Coated with a Biocompatible Coating Having a Negative Surface Charge Gold nanoparticles were prepared as described in example 1 (same gold inorganic core).

A 0.22 μm filtration on PES membrane filter was performed and gold concentration in suspension was determined by a UV-visible spectroscopy assay at 530 nm.

A biocompatible surface coating was performed using meso-2, 3-dimercaptosuccinic acid (DMSA). A sufficient amount of DMSA was added to the nanoparticles' suspension to reach at least half a monolayer coverage (2.5 molecules/nm$^2$) on the surface. pH was adjusted between 7 and 7.2, and the nanoparticles' suspension was stirred overnight.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration: [Au]=0.1 g/L). The hydrodynamic diameter of the so obtained nanoparticles in suspension was equal to 76 nm, with a polydispersity index (dispersion of the nanoparticles' population in size) of 0.46.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [Au]=0.1 g/L). The zeta potential at pH 7 was found equal to −23 mV.

Example 3. Nanoparticles Prepared with an Insulator Material Having a Low Relative Dielectric Constant Equal to or Below 100: Synthesis of Zirconium Oxide Nanoparticles Coated with a Biocompatible Coating Having a Neutral Surface Charge Zirconium oxide (ZrO$_2$) nanoparticles were synthesized by precipitation of zirconium chloride (ZrCl$_4$) with tetramethyl ammonium hydroxide (TMAOH) at a basic pH. The resulting suspension was transferred in an autoclave and heated at a temperature above 110° C. After cooling, the suspension was washed with deionized water and acidified.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 10 nm and 8 nm-12 nm respectively. 446 nanoparticles were counted and their largest dimension was measured.

A 0.22 μm filtration on PES membrane filter was performed and (ZrO$_2$) nanoparticles' concentration was determined by drying the aqueous solution into a powder and weighing the as-obtained mass. A biocompatible coating was prepared using silane-poly(ethylene) glycol 2 kDa ("Si-PEG 2 kDa"). A sufficient amount of "Si-PEG 2 kDa" was added to the nanoparticles' suspension to reach at least half a monolayer coverage (2.5 molecules/nm$^2$) on the surface. The nanoparticles' suspension was stirred overnight and subsequently the pH was adjusted to 7.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the ZrO$_2$ constituting the nanoparticle's core: [ZrO$_2$]=0.1 g/L). The nanoparticles' hydrodynamic diameter was found equal to 55 nm, with a polydispersity index (dispersion of the nanoparticles' population in size) of 0.1.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [ZrO$_2$]=0.1 g/L). The zeta potential at pH7 was found equal to −1 mV.

Example 4. Nanoparticles Prepared with an Insulator Material Having a Low Relative Dielectric Constant Equal to or Below 100: Synthesis of Zirconium Oxide Nanoparticles Coated with a Biocompatible Coating Having a Negative Surface Charge Zirconium oxide nanoparticles were prepared as described in example 3 (same inorganic core).

A 0.22 μm filtration on PES membrane filter was performed and the (ZrO$_2$) nanoparticles' concentration was determined by drying the aqueous suspension to a powder and weighing the as-obtained mass. Surface functionalization was performed using sodium hexametaphosphate. A sufficient mass of sodium hexametaphosphate was added to the nanoparticles' suspension to reach at least half a monolayer coverage (2.5 molecules/nm$^2$) on the surface. The nanoparticles' suspension was stirred overnight and pH was subsequently adjusted to 7.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the ZrO$_2$ constituting the nanoparticle's core: [ZrO$_2$]=0.1 g/L). The nanoparticles' hydrodynamic diameter was found equal to 70 nm, with a polydispersity index (dispersion of the nanoparticles population in size) of 0.11.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [ZrO$_2$]=0.1 g/L). The zeta potential at pH 7 was found equal to −33 mV.

Example 5. Nanoparticles Prepared with a Semiconductor Material: Silicon (Si) Nanoparticles Coated with a Biocompatible Coating Having a Negative Surface Charge Silicon (Si) nanoparticles (powder) were obtained from US Research Nanomaterials Inc. They were coated with PVP (1% wt), representing less than 0.1 molecule/nm$^2$ on the surface.

They were dispersed in water at 30 g/L under sonication (with a probe).

A 0.22 μm filtration on PES membrane filter was performed and the (Si) nanoparticles' concentration was determined by drying the suspension to a powder and weighing the as-obtained mass.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration final concentration of the Si constituting the nanoparticle's core: [Si]=0.1 g/L). The nanoparticles' hydrodynamic diameter was found equal to 164 nm, with a polydispersity index (dispersion of the nanoparticles' population in size) of 0.16.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 53 nm and 45-61 nm respectively. Seventy-one (71) nanoparticles were counted and their largest dimension was measured.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [Si]=0.1 g/L). The zeta potential at pH 7 was found equal to −19 mV.

Example 6. Nanoparticles Prepared with an Insulator Material Having a High Relative Dielectric Constant Equal to or Above 200: Barium Titanate Nanoparticles Coated with a Biocompatible Coating Having a Negative Surface Charge Barium titanate ($BaTiO_3$) nanoparticles' suspension (20% wt in water) was obtained from US Research Materials Inc. (US3835).

Surface functionalization was performed using Silane-poly(ethylene) glycol 10 kDa ("Si-PEG 10 kDa"). Briefly, "Si-PEG 10 kDa" was first dissolved in an ethanol/water solution (⅓ v/v) and added to the $BaTiO_3$ suspension (20% wt in water) to achieve a full monolayer coverage on the surface of the nanoparticles. The suspension was sonicated and subsequently stirred overnight. After a 0.22 μm filtration (filter membrane: poly(ether sulfone)), a washing step was performed in order to eliminate unreacted "Si-PEG 10 kDa" polymers.

The hydrodynamic diameter (measure in intensity) was determined by Dynamic Light Scattering (DLS) at room temperature (about 25° C.), with a Nano-Zetasizer (Malvern) at a scattering angle of 173° with a laser emitting at 633 nm, by diluting the nanoparticles' suspension in water (final concentration of the $BaTiO_3$ constituting the nanoparticle's core: [$BaTiO_3$]=0.1 g/L). The nanoparticles' hydrodynamic diameter was found equal to 164 nm, with a polydispersity index (dispersion of the nanoparticles' population in size) of 0.16.

The zeta potential was determined by measuring the electrophoretic mobility of the nanoparticles (Nano-Zetasizer, Malvern) by diluting the nanoparticles' suspension in a NaCl solution at 1 mM at pH 7 (final concentration: [$BaTiO_3$]=0.1 g/L). The zeta potential at pH 7 was found at −11 mV.

The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates were evaluated using transmission electron microscopy and found equal to 67 nm and 60-77 nm respectively. Fifty-one (51) nanoparticles were counted and their largest dimension was measured.

Example 7. Evaluation of the Prevention/Rescue Efficacy of Nanoparticles from Examples 1, 2, 5 and 6, on $MPP^+$-Induced Neuronal Networks Using the Phenotypic Mea Screening Technology The prevention/rescue efficacy of nanoparticles of the invention was tested on $MPP^+$-treated mouse ventral midbrain/cortex co-cultures, cultured on a 48-wells MEA for 3 weeks. This model represents an in vitro Parkinson's model for screening compounds, based on the functional rescue of dopaminergic neurons using challenged midbrain/cortex cultures growing on MEAs. Midbrain is a region of the brain including the substantia nigra which is part of the basal ganglia and which contains most of the dopaminergic neurons. The evaluation of the nanoparticles' prevention/rescue effect was performed via the measurement of the extracellular electrical activity of the co-culture of neurons plated on Microelectrode Array (MEA) chips.

The induction of a parkinsonian phenotype in mouse neurons in vitro was performed with 1-methyl-4-phenyl pyridinium iodide ($MPP^+$). There is strong evidence that mitochondrial impairment plays a role in the pathogenesis of Parkinson's disease (PD). $MPP^+$ was found to be mitochondrial poison that inhibits cellular respiration through the blockade of the electron transport enzyme complex I (NADH: ubiquinone oxidoreductase). Several laboratories have reported that there is a selective defect in complex I of mitochondrial electron transport chain in the substantia nigra of postmortem tissue of PD patients, and there is also reduction of complex I activity in platelets of patients with early PD. Drugs such as glial cell-derived neurotrophic factor (GDNF), act as neuroprotector agents to prevent/rescue the effect of $MPP^+$ with good preclinical outcomes. GDNF is frequently used as reference in experimental preclinical protocols (Peng J. et al., *Journal of Biomolecular screening*, 2013, 18(5), 522-533: *Using human pluripotent stem cell-derived dopaminergic neurons to evaluate candidate Parkinson's disease therapeutic agents in MPP+ and rotenone models.*).

Material and Methods

Primary Cell Culture, Treatment Conditions

Midbrain and frontal cortex tissue was harvested from embryonic day 14.5 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 μl drop of DMEM containing laminin (10 μg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum.

In the "Nanoparticles" groups, wells were treated at day 7 with nanoparticles' suspension from examples 1 ([Au]=800 μM), 2 ([Au]=800 μM), 5 ([Si]=800 μM) and with nanoparticles' suspension from example 6 ([$BaTiO_3$]=2000 μM), followed by 20 μM of $MPP^+$ at day 8. In the "Control" group, water was added to the wells at day 7, followed by water addition at day 8. In the "$MPP^+$" group, water was added to the wells at day 7, followed by 20 μM of $MPP^+$ at day 8. In the "Reference" group, GDNF (20 ng/ml) was added to the wells at day 7, followed by 20 μM of $MPP^+$ at day 8.

Twenty-four (24) hours following $MPP^+$ (or water for "Control" group) addition, the medium was changed to achieve wash out of $MPP^+$. Medium was subsequently changed twice per week and GDNF was added for the "Reference" group only, at each medium change.

At day 21, 120 minutes of neuronal activity were recorded, and 30 minutes of stable activity were analyzed (FIG. 6).

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel MAESTRO recording system by Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events (FIG. 7).

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

Changes in "general activity parameters" describe the effects on action potential firing rate (spike rate), burst rate, and burst period as the time between the bursts.

"Burst structure parameters" define not only the internal structure of spikes within a high-frequency spiking phase ("burst"), e.g., spike frequency in bursts, spike rate in bursts, and burst spike density, but also the overall structure of the burst, such as duration, area, and plateau.

"Oscillatory parameters" quantify the regularity of occurrence or structure of bursts, which is calculated by coefficients of variation of primary activity parameters describing the variability of parameters (general activity, burst structure) within experimental episodes (Gramowski A. et al., *Eur. J. Neurosci.*, 2004, 19, 2815-2825: *Substance identification by quantitative characterization of oscillator activity in murine spinal cord networks on microelectrode arrays*). Higher values indicate less regular burst structure or less regular general activity (e.g., spiking, bursting).

As a measure of synchronicity in the spike trains, "CVnet parameters" reflect "synchronization" among neurons within the network (Gramowski A. et al., *Eur. J. Neurosci.*, 2004, 19, 2815-2825: *Substance identification by quantitative characterization of oscillator activity in murine spinal cord networks on microelectrode arrays*). CVnet is the coefficient of variation over the network. Large CVnet values imply a wide range of variation in the activity across the network, meaning less synchronization. (Gramowski A. et al., *Frontiers in Neurology*, 2015, 6(158): *Enhancement of cortical network activity in vitro and promotion of GABAergic neurogenesis by stimulation with an electromagnetic field with* 150 *MHz carrier wave pulsed with an alternating* 10 *and* 16 *Hz modulation*).

Functional effects induced by $MPP^+$ on neuronal network and prevention/rescue efficacy of the nanoparticles of the invention were evaluated through the above described parameters (also recapitulated for some of them in the Table 2 below).

TABLE 2

Activity-describing parameters from the multiparametric data analysis in the following three categories: general activity, oscillatory behavior and synchronicity.

| | | |
|---|---|---|
| General activity | Spike rate | Number of spikes per second, averaged over all spike trains recorded |
| Oscillatory behavior | Burst rate SD (bursting regularity) | Standard deviation of number of bursts per minute, indicating the variability of burstiness of units within experimental episodes |
| | Burst area SD (burst structure regularity) | Standard deviation of area under the curve after integrating the bursts, defined by burst duration, number of spikes in bursts, spike frequency in bursts. The parameter describes the variability of burst area within experimental episodes. Higher values indicate less regular burst structure |
| | Burst spikes' number SD (bursting structure regularity) | Standard deviation of spikes' number in bursts describes the variation of a single unit spikes' number in bursts within experimental episodes. Lower values are a measure indicating lower degree of variation in burst spikes' number, therewith more regular structure. |
| Synchronicity | Simplex (spiking complexity) | For spike simplex calculation, the spikes' trains are divided into timeframes of 1 ms bin-size. Within those bins, different units within the network generate spikes. All units exhibiting a spike are defined as one simplex. The outcome of the quantity of all simplex is the spike simplex. It is a measure for connectivity and complexity in neuronal network. Higher values reflect higher synchronicity among neurons. |

Values related to spontaneous native activity at day 21 were derived from 60 seconds bin data taken from a 30 minutes span after a 30 minutes stabilization of activity. Results (parameter values) were expressed as mean±SEM of independent networks. For each "Nanoparticles" group, at least 8 active wells, for the "Control" group, at least 30 active wells, and for the "MPP+" group, at least 26 active wells ("active" meaning wells with a sufficient number of electrodes measuring electrical activity) were included in the analysis. The absolute parameters' distributions were tested for normality and the statistical significance between groups was assessed via one-way ANOVA.

FIGS. 8 and 9 present some representative parameters from the following categories: general activity, oscillatory behavior and synchronicity. These parameters characterize MPP+-induced functional effects and the prevention/rescue efficacy of the nanoparticles of the invention or of GDNF (i.e. the ability to prevent/rescue functional effects to a level similar to that of "Control" group).

To evaluate compound effects, multiparametric results of a selection of 204 parameters were projected into a single parameter termed the "Effect Score". It is a linear combination of selected features, transforming the datasets onto a vector with "Control" group at a mean value of "0" and "MPP+" group at a mean value of "1". Calculation of the Z-factor of the Effect Score was performed through feature selection of 18 out of the 204 parameters measured, optimized to find the best discrimination between the "Control" group and the "MPP+" group (Kümmel A, et al., *J Biomol Screen.*, 2010, 15(1), 95-101: *Integration of multiple readouts into the z' factor for assay quality assessment*).

The Effect Score analysis is shown in FIG. 10.

The prevention/rescue efficacy of the nanoparticles of the invention is shown in Table 3.

TABLE 3

Summary of Effect Score and prevention/rescue efficacy of nanoparticles of the invention (from examples 1, 2, 5 and 6) or of GDNF, on MPP+-induced effects on neuronal network.

| Group | Effect Score | Prevention/ rescue efficacy |
|---|---|---|
| "Control" group | 0 | Reference (set at 100%) |
| "MPP+" group | 1 | 0% |
| "Nanoparticles" group: biocompatible gold nanoparticles from example 1 | 0 | 100% |
| "Nanoparticles" group: biocompatible gold nanoparticles from example 2 | 0.22 | 78% |
| "Nanoparticles" group: biocompatible Si nanoparticles from example 5 | 0.49 | 51% |
| "Nanoparticles" group: biocompatible BaTiO$_3$ nanoparticles from example 6 | 0.39 | 61% |
| "Reference" group: GDNF | 0.44 | 56% |

FIGS. 8, 9 and 10 and table 3 show that pretreatment of the neuronal network with nanoparticles of the invention prevents/rescues MPP+ induced functional effects on the neuronal network. Interestingly, the prevention/rescue efficacy is observed for parameters in categories related to oscillatory behavior and synchronicity and it can reach a level up to what is observed in "Control" group. These oscillatory behavior and synchronization parameters are typically monitored as a measure of altered network development. These parameters can advantageously be rescued in presence of the nanoparticles of the invention.

These results highlight the ability of the nanoparticles described in the present application to prevent/rescue MPP+ induced functional effects on the neuronal network.

Example 8: Evaluation of the Effects of the Nanoparticles from Examples 1, 2, 3, 4, 5 and 6 on Amyloid Beta 1-42-Induced Functional Effects on Primary Mouse Neuronal Networks Using the Phenotypic MEA Screening Technology The rescue efficacy of nanoparticles of the invention was tested in vitro via MEAs on an amyloid beta 1-42 (Abeta 1-42)-induced model of Alzheimer's disease in frontal cortex cultures of mouse neurons. β-Amyloid peptide 1-42, the principal constituent of the neurotic plaques seen in Alzheimer disease (AD) patients, is known to trigger excess amount of glutamate in the synaptic cleft by inhibiting the astroglial glutamate transporter and to increase the intracellular $Ca^{2+}$ level through enhancement of N-methyl-D-aspartate (NMDA) receptor activity. Other mechanisms leading to excitotoxicity may include the induction of oxidative stress and the direct impact of abeta on the glutamatergic NMDA receptor. Whatever the precise underlying pathogenic processes, overstimulation of the nerve cell by glutamate and intracellular calcium accumulation will eventually cause neuronal apoptosis, disrupt synaptic plasticity and as a result of such dysregulation will profoundly impair learning and memory function (Nyakas C. et al., *Behavioural Brain Research*, 2011, 221, 594-603: *The basal forebrain cholinergic system in aging and dementia. Rescuing cholinergic neurons from neurotoxic amyloid-β42 with memantine.*). Currently, FDA-approved anti AD drugs are limited to acetylcholinesterase (AChE) inhibitors and NMDA receptor antagonists. Traditional AChE inhibitors include donepezil which mainly act on the central action site of AChE.

Material and Methods

Primary Cell Culture

Frontal cortex tissue was harvested from embryonic day 15/16 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 μl drop of DMEM containing laminin (10 μg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum. The developing co-cultures were treated with the mitosis inhibitors 5-fluoro-2'-deoxyuridine (25 μM) and uridine (63 μM) on day 5 after seeding to prevent further glial proliferation.

To induce an Alzheimer-related functional phenotype, synthetic HFIP (hexafluoroisopropanol)-treated Abeta 1-42 peptides (HFIP treatment produces monomers of amyloid beta) were used at a sub-toxic dose (100 nM).

In the "Nanoparticles" groups, wells were first treated with Abeta 1-42 (synthetic HFIP-treated Amyloid-beta 1-42 peptides) at T0 (T0 being at the end of the 28 days-in vitro culture period). Wells were then treated at T0+4 hours with the nanoparticles' suspension from examples 1 ([Au]=800 μM), 2 ([Au]=800 μM), 3 ([ZrO$_2$]=800 μM), 4 ([ZrO$_2$]=800

μM), 5 ([Si]=800 μM) and from example 6 ([BaTiO$_3$]=2000 μM), in independent and parallel experiments. In the "Control" group, water was added to the wells at T0, and then at T0+4 hours. In the "Abeta" group, Abeta 1-42 was added to the wells at T0, and then water was added to the wells at T0+4 hours. In the "Reference" group, Abeta 1-42 was added to the wells at T0, and donepezil (300 nM) was added to the wells at T0+4 hours.

Neuronal activity was recorded as follows (cf. FIG. 11):

At T0, prior Abeta 1-42 addition (or water in the "Control" group)

At T0 30 1 h, T0+2 h, T0+3 h, T0+4 h (prior addition of the nanoparticles in the «Nanoparticles» group, or donepezil in the "Reference" group, or "water" in the Control group), T0+5 h and T0+6 h.

Values were derived from 60 seconds bin data taken from a 30 minutes span after a 30 minutes stabilization of activity.

Microelectrode Array Neurochips

The 48 wells microelectrodes array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel MAESTRO recording system from Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$. The action potentials, or "spikes", were recorded in spike trains and were clustered in so-called "bursts". Bursts were quantitatively described via direct spike train analysis using the programs Spike Wrangler and NPWaveX (both Neuro-Proof GmbH, Rostock, Germany). Bursts were defined by the beginning and end of short spike events.

With a multiparametric high-content analysis of the network activity patterns, 204 activity-describing spike train parameters were extracted. These parameters allow obtaining a precise description of activity changes in the four categories as follows: general activity, burst structure, oscillatory behavior and synchronicity.

Functional effects of amyloid beta 1-42 on neuronal network and rescue efficacy of functional effects of the neuronal network by the nanoparticles of the invention were evaluated through the above described parameters (also recapitulated for some of them in Table 4 below).

TABLE 4

Activity-describing parameters from the multiparametric data analysis in the following four categories: general activity, burst structure, oscillatory behavior and synchronicity

| | | |
|---|---|---|
| General activity | Spike contrast | Describes the occurrence or absence of spikes in neighboring time segments of the spike train, reflecting the variability in burstiness of units within experimental episodes |
| Burst structure | Burst area | Area under the curve integrating the bursts, defined by burst duration, number of spikes in the bursts, spikes' frequency in bursts |
| Oscillatory behavior | Burst shape count3 CVtime | Each burst is separated in three intervals by use of their gravitational centers. Count is the ratio of spikes of each of these intervals to the total number of spikes in each burst. This parameter describes the coefficient of variation over time of the distribution of spikes within bursts |
| Synchronicity | Burst shape fast CVnet | Coefficient of variation over the network of the fraction of bursts characterized by fast onset of action. Higher values indicate a lower synchronicity of burst shape within experimental episode |

Values related to spontaneous native activity were derived from 60 seconds bin data taken from a 30 minutes span after a 30 min stabilization of activity. Results (parameter values) were expressed as mean±SEM of independent networks. For each "Nanoparticles" group, at least 9 active wells, for the "Control" group, at least 18 active wells, and for the "Abeta" group, at least 18 active wells ("active" meaning wells with a sufficient number of electrodes measuring electrical activity), were included in the analysis. The absolute parameters' distributions were tested for normality and the statistical significance between groups was assessed via one-way ANOVA.

FIG. 12 shows some representative parameters from the following categories: general activity, burst structure, oscillatory behavior and synchronicity, characterizing Abeta 1-42 functional effects and the rescue efficacy allowed by the nanoparticles of the invention or by donepezil (i.e. ability to rescue functional effects to a level similar to that of the "Control" group).

To evaluate compound effects, multiparametric results of a selection of 204 parameters were projected into a single parameter termed the "Effect Score". It is a linear combination of selected features, transforming the datasets onto a vector with "Control" group at a mean value of "0" and "Abeta" group at a mean value of "1". Calculation of the Z-factor of the Effect Score was performed through feature selection of 15 out of the 204 parameters measured, optimized to find the best discrimination between the "Control" group and the "Abeta" group (Kümmel A, et al., *J Biomol Screen.*, 2010, 15(1), 95-101: *Integration of multiple readouts into the z' factor for assay quality assessment.*).

The Effect Score analysis is shown in FIG. 13.

The rescue efficacy of the nanoparticles of the invention is shown in Table 5.

TABLE 5

Summary of Effect Score and rescue efficacy of the nanoparticles of the invention or of donepezil, on Abeta 1-42-induced effects on the neuronal network.

| Group | Effect Score | Rescue efficacy |
|---|---|---|
| "Control" group | 0 | Reference (set at 100%) |
| "Abeta" group | 1 | 0% |
| "Nanoparticles" group: biocompatible gold nanoparticles from example 1 | 0.24 | 76% |
| "Nanoparticles" group: biocompatible gold nanoparticles from example 2 | 0.61 | 39% |
| "Nanoparticles" group: biocompatible zirconium oxide nanoparticles from example 3 | 0.40 | 60% |
| "Nanoparticles" group: biocompatible zirconium oxide nanoparticles from example 4 | 0.49 | 51% |
| "Nanoparticles" group: biocompatible silicon nanoparticles from example 5 | 0.46 | 54% |
| "Nanoparticles" group: biocompatible BaTiO$_3$ nanoparticles from example 5 | 0.36 | 64% |
| Donepezil | 0.46 | 54% |

FIGS. 12 and 13 and Table 5 show that treatment of the neuronal network with the nanoparticles of the invention rescues Abeta 1-42 induced functional effects on the neuronal network. The rescue efficacy is observed for parameters in categories related to oscillatory behavior and synchronicity and it can advantageously reach a level up to what is observed in the "Control" group. These oscillatory behavior and synchronization parameters are classically evaluated to detect an altered network development. Oscillatory behavior and synchronization can be rescued in presence of the nanoparticles of the invention.

These results highlight the advantageous performances of the nanoparticles described in the present application in rescuing Abeta 1-42 induced functional effects on the neuronal network.

Example 9: Synthesis and Physico-Chemical Characterization of Gold Nanoparticles with Different Sizes Having a Neutral Surface Charge Gold nanoparticles are obtained by reduction of gold chloride with sodium citrate in aqueous solution. Protocol was adapted from G. Frens *Nature Physical Science* 241 (1973) 21.

In a typical experiment, HAuCl$_4$ solution is heated to boiling. Subsequently, sodium citrate solution is added. The resulting suspension is maintained under boiling for an additional period of 5 minutes. The nanoparticle size is adjusted from about 15 nm up to about 110 nm by carefully modifying the citrate versus gold precursor ratio (cf. Table 6).

The as prepared gold nanoparticles suspension is then concentrated using an ultrafiltration device (Amicon stirred cell model 8400 from Millipore) with cellulose membrane having an appropriate molecular weight cut-off (MWCO) and filtered through a 0.22 μm cutoff membrane filter (PES membrane from Millipore) under laminar hood.

A surface coating is performed using α-methoxy-ω-mercaptopoly(ethylene glycol) 20 kDa ("thiol-PEG20 kDa"). A sufficient amount of "thiol-PEG 20 kDa" is added to the nanoparticles' suspension to obtain a monolayer coverage on the gold nanoparticle surface. pH is adjusted between 6.8 and 7.4, and the nanoparticles' suspension is stirred overnight. Excess of thiol-PEG 20 kDa is removed using a ultrafiltration centrifugal filter (Vivaspin from Sartorius or Amicon Ultra from Merck Millipore) with an appropriate MWCO membrane under laminar hood and the final suspension is stored at 4° C. Particle size is determined using transmission electronic microscopy by counting at least 200 nanoparticles, taking the largest nanoparticle dimension for size measurement. The median largest size of the core of the nanoparticles or nanoparticles' aggregates of the population and the size of the core of the nanoparticles or nanoparticles' aggregates representing the 30%-70% percentile of the population of nanoparticles and nanoparticles' aggregates are reported in table 6 together with the concentration of gold ([Au]) measured by Inductively-Coupled Optical Emission Spectroscopy (ICP-OES) and the zeta potential determined by measuring the electrophoretic mobility of the nanoparticles (Nano-Zetasizer, Malvern) by diluting the nanoparticles' suspension in a NaCl solution at 1 mM, at a gold concentration ([Au]) between 0.01 and 0.05 g/L and at pH about 7.

TABLE 6

| Samples | Synthesis Ratio Citrate/Au (mol/mol) | Median largest size of the core of the nanoparticle (nm) | 30%-70% percentile (nm) | Zeta potential (mV) | [Au] mg/mL (by ICP-OES) |
| --- | --- | --- | --- | --- | --- |
| GOLD-15 | 3.5 | 15 | 14-16 | −3 | 3.6 |
| GOLD-30 | 1.96 | 34 | 30-37 | −3 | 3.9 |
| GOLD-45 | 1.26 | 45 | 42-49 | −4 | 3.6 |
| Same nanoparticles core as nanoparticles from examples 1 & 2 | | | | | |
| GOLD-80 | 0.8 | 83 | 77-93 | −2 | 3.4 |
| GOLD-110 | 0.7 | 108 | 91-123 | −2 | 2.9 |

FIG. 14 shows representative transmission electronic microscopy (TEM) images of the gold nanoparticles described in table 6.

Example 10. Evaluation of the Prevention/Rescue Efficacy of Nanoparticles GOLD-15 and GOLD-45 from Example 9, on MPP$^+$-Induced Neuronal Networks Using the Phenotypic MEA Screening Technology The prevention/rescue efficacy of nanoparticles of the invention was tested on MPP$^+$-treated mouse ventral midbrain/cortex co-cultures, cultured on a 48-wells MEA for 3 weeks. The evaluation of the nanoparticles' prevention/rescue effect was performed via the measurement of the extracellular electrical activity of the co-culture of neurons plated on Microelectrode Array (MEA) chips. The induction of a parkinsonian phenotype in mouse neurons in vitro was performed with 1-methyl-4-phenyl pyridinium iodide (MPP$^+$).

Material and Methods
Primary Cell Culture, Treatment Conditions
Midbrain and frontal cortex tissue was harvested from embryonic day 14.5 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 μl drop of DMEM containing laminin (10 μg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum.

In the "Nanoparticles" groups, wells were treated at day 7 with nanoparticles' suspension ([Au]=310 +/−40 μM) from example 9 (GOLD-15 and GOLD-45), followed by 20 μM of MPP$^+$ at day 8. In the "Control" group, water was added to the wells at day 7, followed by water addition at day 8. In the "MPP$^+$" group, water was added to the wells at day 7, followed by 20 μM of MPP$^+$ at day 8.

Twenty-four (24) hours following MPP$^+$ (or water for "Control" group) addition, the medium was changed to achieve wash out of MPP$^+$. Medium was subsequently changed twice per week. At day 21, 120 minutes of neuronal activity were recorded, and 30 minutes of stable activity were analyzed.

Microelectrode Array Neurochips
The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel recording system from Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes), were recorded as spike trains, which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events.

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

Functional effects induced by MPP on neuronal network and prevention/rescue efficacy of the nanoparticles of the invention were evaluated through the above described parameters.

Values related to spontaneous native activity at day 21 were derived from 60 seconds bin data taken from a 30 minutes span after a 30 minutes stabilization of activity. Results (parameter values) were expressed as mean±SEM of independent networks. For each "Nanoparticles" group, the "Control" group, and the "MPP$^+$" group, at least 19 active wells ("active" meaning wells with a sufficient number of electrodes measuring electrical activity) were included in the analysis. The absolute parameters' distributions were tested for normality and the statistical significance between groups was assessed via one-way ANOVA.

To evaluate compound effects, multiparametric results of a selection of 204 parameters were projected into a single parameter termed the "Effect Score". It is a linear combination of selected features, transforming the datasets onto a vector with "Control" group at a mean value of "0" and "MPP$^+$" group at a mean value of "1". Calculation of the Z-factor of the Effect Score was performed through feature selection of 20 out of the 204 parameters measured, optimized to find the best discrimination between the "Control" group and the "MPP⁺" group (Kümmel A, et al., *J Biomol Screen.*, 2010, 15(1), 95-101: *Integration of multiple readouts into the z' factor for assay quality assessment*).

The Effect Score analysis is shown in FIG. 15.

The prevention/rescue efficacy of the nanoparticles of the invention is shown in Table 7.

TABLE 7

Summary of Effect Score and prevention/rescue efficacy of nanoparticles of the invention (GOLD-15 and GOLD-45 from examples 9), on MPP⁺-induced effects on neuronal network.

| Group | Effect Score | Prevention/rescue efficacy |
|---|---|---|
| "Control" group | 0 | Reference (set at 100%) |
| "MPP⁺" group | 1 | 0% |
| "Nanoparticles" group: biocompatible gold nanoparticles GOLD-45 from example 9 | 0.14 | 86% |
| "Nanoparticles" group: biocompatible gold nanoparticles GOLD-15 from example 9 | 0.46 | 54% |

FIG. 15 and table 7 show that pretreatment of the neuronal network with nanoparticles of the invention prevents/rescues MPP⁺ induced functional effects on the neuronal network. Interestingly, the gold nanoparticles with the median largest size of the core of the nanoparticles of the population equal to 15 nm are less efficient in preventing/rescuing MPP induced functional effects on the neuronal network than are gold nanoparticles having a median largest size of the core of the nanoparticles of the population equal to 45 nm.

These results highlight the ability of both gold nanoparticles to prevent/rescue MPP⁺ induced functional effects on the neuronal network, with gold nanoparticles with median largest size of 45 nm being more efficient than gold nanoparticles with median largest size of 15 nm.

Example 11. Synthesis of Nanoparticles Prepared with a Conductor Material: Poly(3,4-Ethylenedioxythiophene) Nanoparticles (PEDOT Nanoparticles) Having a Negative Surface Charge Poly(3,4-ethylenedioxythiophene) nanoparticles (PEDOT nanoparticles) dispersion in water (1.1% w/w) were obtained from Sigma (sigma 675288) and used as such.

The zeta potential was determined by measuring the electrophoretic mobility of the nanoparticles (Nano-Zetasizer, Malvern) by diluting the nanoparticles' suspension in a NaCl solution at 1 mM at pH 7.3 (final PEDOT concentration: 1 g/L). The zeta potential at pH 7.3 was found equal to −53 mV.

The median largest dimension of the nanoparticles or nanoparticles' aggregates of the population and the size of the core of the nanoparticles or nanoparticles' aggregates representing the 30%-70% percentile of the population of nanoparticles and nanoparticles' aggregates were evaluated using scanning electron microscopy (SEM) and were equal to 408 nm and 311 nm-518 nm respectively (56 nanoparticles were counted and their largest dimension was measured).

Example 12. Evaluation of the Prevention/Rescue Efficacy of PEDOT Nanoparticles from Example 11 on MPP⁺-Induced Neuronal Networks Using the Phenotypic MEA Screening Technology The prevention/rescue efficacy of nanoparticles of the invention was tested on MPP⁺-treated mouse ventral midbrain/cortex co-cultures, cultured on a 48-wells MEA for 3 weeks. The evaluation of the nanoparticles' prevention/rescue effect was performed via the measurement of the extracellular electrical activity of the co-culture of neurons plated on Microelectrode Array (MEA) chips.

The induction of a parkinsonian phenotype in mouse neurons in vitro was performed with 1-methyl-4-phenyl pyridinium iodide (MPP⁺).

Material and Methods

Primary Cell Culture, Treatment Conditions

Midbrain and frontal cortex tissue was harvested from embryonic day 14.5 chr:NMRI mice (Charles River). Mice were sacrificed by cervical dislocation. Tissue was dissociated by enzymatic digestion (133.3 Kunitz units/ml DNase; 10 Units/ml Papain) and mechanical trituration, counted, vitality controlled, and plated in a 20 µl drop of DMEM containing laminin (10 µg/ml), 10% fetal bovine serum and 10% horse serum on MEAs. Cultures on MEAs were incubated at 37° C. in a 10% $CO_2$ atmosphere until ready for use. Culture media were replenished two times a week with DMEM containing 10% horse serum.

In the "Nanoparticles" groups, wells were treated at day 7 with nanoparticles' suspension ([PEDOT]=500 µM) from example 11, followed by 20 µM of MPP⁺ at day 8. In the "Control" group, water was added to the wells at day 7, followed by water addition at day 8. In the "MPP⁺" group, water was added to the wells at day 7, followed by 20 µM of MPP⁺ at day 8.

Twenty-four (24) hours following MPP⁺ (or water for "Control" group) addition, the medium was changed to achieve wash out of MPP⁺. Medium was subsequently changed twice per week.

At day 21, 120 minutes of neuronal activity were recorded, and 30 minutes of stable activity were analyzed.

Microelectrode Array Neurochips

The 48 wells microelectrode array neurochips were purchased from Axion Biosystems Inc. These chips have 16 passive electrodes per well. The surface was coated for 1 hour with Polyethyleneimine (PEI, 50% in Borate buffer), washed and air-dried.

Multichannel Recording and Multiparametric Data Analysis

For the recording, the multichannel MAESTRO recording system by Axion Biosystems (USA) was used. For extracellular recording, 48-wells MEAs were placed into the MAESTRO recording station and maintained at 37° C. Recordings were made in DMEM/10% heat inactivated horse serum. The pH was maintained at 7.4 with a continuous stream of filtered, humidified airflow with 10% $CO_2$.

Each unit represents the activity originating from one neuron recorded at one electrode. Units are separated at the beginning of the recording. For each unit, action potentials (i.e. spikes) were recorded as spike trains which are clustered in so-called "bursts". Bursts were quantitatively described via direct spike train analysis using the programs Spike Wrangler and NPWaveX (both NeuroProof GmbH, Rostock, Germany). Bursts were defined by the beginning and end of short spike events.

With a multiparametric high-content analysis of the network activity patterns, 204 activity-describing spike train parameters were extracted. These parameters allow obtaining a precise description of activity changes in the following four categories: general activity, burst structure, oscillatory behavior and synchronicity.

Functional effects induced by MPP on neuronal network and prevention/rescue efficacy of the nanoparticles of the invention were evaluated through the above described parameters.

Values related to spontaneous native activity at day 21 were derived from 60 seconds bin data taken from a 30 minutes span after a 30-90 minutes stabilization of activity. Results (parameter values) were expressed as mean±SEM of independent networks. For the "Nanoparticles" group, at least 5 active wells, for the "Control" group, at least 20 active wells, and for the "MPP+" group, at least 20 active wells ("active" meaning wells with a sufficient number of electrodes measuring electrical activity) were included in the analysis. The absolute parameters' distributions were tested for normality and the statistical significance between groups was assessed via one-way ANOVA.

To evaluate compound effects, multiparametric results of a selection of 204 parameters were projected into a single parameter termed the "Effect Score". It is a linear combination of selected features, transforming the datasets onto a vector with "Control" group at a mean value of "0" and "MPP+" group at a mean value of "1". Calculation of the Z-factor of the Effect Score was performed through feature selection of 20 out of the 204 parameters measured, optimized to find the best discrimination between the "Control" group and the "MPP+" group (Kümmel A, et al., *J Biomol Screen.*, 2010, 15(1), 95-101: *Integration of multiple readouts into the z' factor for assay quality assessment*).

The Effect Score analysis is shown in FIG. 17.

The prevention/rescue efficacy of the nanoparticles of the invention is shown in Table 8.

TABLE 8

Summary of Effect Score and prevention/rescue efficacy of PEDOT nanoparticles of the invention (from example 11), on MPP+-induced effects on neuronal network.

| Group | Effect Score | Prevention/rescue efficacy |
|---|---|---|
| "Control" group | 0 | Reference (set at 100%) |
| "MPP+" group | 1 | 0% |
| "Nanoparticles" group: biocompatible PEDOT nanoparticles from example 11 | 0.59 | 41% |

FIG. 17 and table 8 show that pretreatment of the neuronal network with PEDOT nanoparticles of the invention prevents/rescues MPP+ induced functional effects on the neuronal network.

These results highlight the ability of the nanoparticles described in the present application to prevent/rescue MPP+ induced functional effects on the neuronal network.

Example 13. Synthesis of Nanoparticles Prepared with an Insulator Material Having a Low Relative Dielectric Constant Equal to or Below 100: Synthesis of Hafnium Oxide Nanoparticles Coated with a Biocompatible Coating Having a Negative Surface Charge Hafnium oxide ($HfO_2$) nanoparticles were synthesized by precipitation of Hafnium chloride ($HfCl_4$) with tetramethyl ammonium hydroxide (TMAOH) at a basic pH. The resulting suspension was transferred in an autoclave and heated at a temperature above 110° C. After cooling, the suspension was washed with deionized water and acidified.

Surface functionalization was performed using sodium hexametaphosphate. A sufficient mass of sodium hexametaphosphate was added to the nanoparticles' suspension to reach at least half a monolayer coverage (2.5 molecules/$nm^2$) on the surface. The nanoparticles' suspension was stirred overnight and pH was subsequently adjusted to 7.

The invention claimed is:

1. A method for preventing or treating a neurological disease selected from Parkinson's disease, Alzheimer's disease, epilepsy, obsessive compulsive disorder, autism spectrum disorder, depression disorder, dystonia, Tourette's syndrome, schizophrenia, stroke, aphasia, dementia, tinnitus, Huntington's disease, essential tremor, bipolar disorder, anxiety disorder, addiction disorder, and consciousness vegetative state, or at least one symptom thereof in a subject, wherein the method comprises a step of administering nanoparticle or nanoparticle aggregate, or a composition comprising nanoparticles and/or nanoparticle aggregates and a pharmaceutically acceptable support, to a subject, the material of the nanoparticle or nanoparticle aggregate being selected from the group consisting of a conductor material that is a metal having a standard reduction potential E° above 0.2 selected from Tl, Po, Ag, Pd, Ir, Pt, Au, and a mixture thereof, or an organic material having contiguous sp2 hybridized carbon centers in its structure, a semiconductor material with a band gap Eg below 3.0 eV selected from a mixed composition of elements from groups III and V of the Mendeleev's periodic table, a mixed composition of elements from groups II and VI of the Mendeleev's periodic table, and an element from group IV-A of the Mendeleev's periodic table, and an insulator material with a dielectric constant $\varepsilon_{ijk}$ equal to or above 200, or an insulator material with a dielectric constant $\varepsilon_{ijk}$ equal to or below 100 selected from $Al_2O_3$, $LaAlO_3$, $La_2O_3$, $SiO_2$, $SnO_2$, $Ta_2O_5$, $ReO_2$, $ZrO_2$, $HfO_2$ and carbon diamond, the relative dielectric constant $\varepsilon^{ijk}$ being measured between 20° C. and 30° C. and between $10^2$ Hz up to the infrared frequency, wherein i) the median largest size of the core of the nanoparticle or nanoparticles' aggregate of the population is of at least 30 nm when the material is a conductor material, a semiconductor material or an insulator material with a dielectric constant $\varepsilon_{ijk}$ equal to or above 200, and wherein ii) the core of the nanoparticle or nanoparticle aggregate is coated with a biocompatible coating providing a neutral or a negative surface charge when measured in a solution of water having a concentration of electrolytes between 0.001 and 0.2 M, the concentration of the nanoparticle or nanoparticle aggregate material is between 0.01 and 10 g/L and a pH between 6 and 8, wherein iii) the method does not include any step of exposing the nanoparticles or nanoparticle aggregates to an electric field nor to any other external activation source, wherein iv) the nanoparticles or nanoparticle aggregates remain in the subject, and wherein v), the nanoparticles or aggregates of nanoparticles is not used as carriers of therapeutic compound(s) or drug(s).

2. The method according to claim 1, wherein the conductor material is selected from Ir, Pd, Pt, Au, and any mixture thereof, and an organic material having contiguous sp2 hybridized carbon centers in its structure, said organic material being selected from polyaniline, polypyrrole, polyacetylene, polythiophene, polycarbazole, polypyrene and any mixture thereof.

3. The method according to claim 1, wherein the nanoparticle's or nanoparticles aggregate's material is an element from group IV-A of the Mendeleev's periodic table and is doped with a charge carrier selected from Al, B, Ga, In and P.

4. The method according to claim 1, wherein the insulator material with a band gap Eg equal to or above 3.0 eV and the relative dielectric constant $\varepsilon_{ijk}$ is-equal to or above 200 is a dielectric material which is a mixed-metal oxide selected from $BaTiO_3$, $KTaNbO_3$, $KTaO_3$, $SrTiO_3$ and $BaSrTiO_3$.

5. The method according to claim 1, wherein the insulator material with a band gap Eg equal to or above 3.0 eV and a relative dielectric constant $\varepsilon_{ijk}$ equal to or below 100 is selected from $ReO_2$, $ZrO_2$ and $HfO_2$.

6. The method according to claim 1, wherein the neurological disease is Parkinson's disease or Alzheimer's disease.

7. The method according to claim 1, wherein the composition comprises at least two distinct nanoparticles and/or nanoparticle aggregates.

8. A composition or kit comprising at least two distinct nanoparticles and/or nanoparticle aggregates, the nanoparticles' or nanoparticles aggregates' material being selected from the group consisting of a conductor material that is a metal having a standard reduction potential E° above 0.2 selected from Tl, Po, Ag, Pd, Ir, Pt, Au, and a mixture thereof, or an organic material having contiguous sp2 hybridized carbon centers in its structure, a semiconductor material with a band gap Eg below 3.0 eV selected from a mixed composition of elements from groups III and V of the Mendeleev's periodic table, a mixed composition of elements from groups II and VI of the Mendeleev's periodic table, and an element from group IV-A of the Mendeleev's periodic table, and an insulator material with a dielectric constant $\varepsilon_{ijk}$ equal to or above 200, and an insulator material with a dielectric constant $\varepsilon_{ijk}$ equal to or below 100 selected from $Al_2O_3$, $LaAlO_3$, $La_2O_3$, $SiO_2$, $SnO_2$, $Ta_2O_5$, $ReO_2$, $ZrO_2$, $HfO_2$ and carbon diamond, the relative dielectric constant $\varepsilon_{ijk}$ being measured between 20° C. and 30° C. and between $10^2$ Hz up to the infrared frequency, wherein i) the median largest size of the core of the nanoparticle or nanoparticle aggregate of the population is of at least 30 nm when the material is a conductor material, a semiconductor material or an insulator material with a dielectric constant $\varepsilon_{ijk}$ equal to or above 200, and wherein ii) the core of the nanoparticle or nanoparticles aggregate is coated with a biocompatible coating providing a neutral or a negative surface charge when measured in a solution of water having a concentration of electrolytes between 0.001 and 0.2 M, the concentration of the nanoparticle or nanoparticle aggregate material is between 0.01 and 10 g/L and a pH between 6 and 8.

9. The method according to claim 1, wherein the element from group IV-A of the Mendeleev's periodic table is silicon (Si) or Germanium (Ge).

* * * * *

UNITED STATES PATENT AND TRADEMARK OFFICE
CERTIFICATE OF CORRECTION

PATENT NO. : 11,497,717 B2
APPLICATION NO. : 16/955092
DATED : November 15, 2022
INVENTOR(S) : Marie-Edith Meyre, Laurent Levy and Agnes Pottier Page 1 of 1

It is certified that error appears in the above-identified patent and that said Letters Patent is hereby corrected as shown below:

In the Specification

Column 43,
Line 33, "MPP" should read --$MPP^+$--.

In the Claims

Column 46,
Line 41, "$\varepsilon^{ijk}$ being" should read --$\varepsilon_{ijk}$ being--.

Signed and Sealed this
Ninth Day of January, 2024

Katherine Kelly Vidal
*Director of the United States Patent and Trademark Office*